United States Patent
Grzelakowski

(10) Patent No.: US 9,994,682 B2
(45) Date of Patent: Jun. 12, 2018

(54) POLYMERS AND PROCESS FOR MAKING MEMBRANES

(71) Applicant: APPLIED BIOMIMETIC A/S, Nordborg (DK)

(72) Inventor: Mariusz Piotr Grzelakowski, Cincinnati, OH (US)

(73) Assignee: APPLIED BIOMIMETIC A/S, Nordborg (DK)

( * ) Notice: Subject to any disclaimer, the term of this patent is extended or adjusted under 35 U.S.C. 154(b) by 130 days.

(21) Appl. No.: 15/128,730

(22) PCT Filed: Mar. 24, 2015

(86) PCT No.: PCT/EP2015/056294
§ 371 (c)(1),
(2) Date: Sep. 23, 2016

(87) PCT Pub. No.: WO2015/144725
PCT Pub. Date: Oct. 1, 2015

(65) Prior Publication Data
US 2017/0166704 A1    Jun. 15, 2017

(30) Foreign Application Priority Data
Mar. 26, 2014    (GB) .................................. 1405391.2

(51) Int. Cl.
| | | |
|---|---|---|
| *C08G 77/452* | (2006.01) | |
| *B01D 69/12* | (2006.01) | |
| *B01D 71/82* | (2006.01) | |
| *B01D 71/70* | (2006.01) | |
| *B01D 71/80* | (2006.01) | |
| *B01D 71/58* | (2006.01) | |
| *C02F 1/44* | (2006.01) | |
| *A61K 9/48* | (2006.01) | |

(52) U.S. Cl.
CPC .......... *C08G 77/452* (2013.01); *A61K 9/4816* (2013.01); *B01D 69/125* (2013.01); *B01D 71/58* (2013.01); *B01D 71/70* (2013.01); *B01D 71/80* (2013.01); *B01D 71/82* (2013.01); *C02F 1/44* (2013.01)

(58) Field of Classification Search
None
See application file for complete search history.

(56) References Cited

U.S. PATENT DOCUMENTS

| | | | |
|---|---|---|---|
| 6,916,488 B1 * | 7/2005 | Meier ................. | A61K 9/5146 424/1.21 |
| 2004/0049230 A1 | 3/2004 | Montemagno et al. | |

(Continued)

OTHER PUBLICATIONS

Isaacman et al, "Stealth Polymeric Vesicles via Metal-Free Click Coupling", Biomacromolecules 2013, 14, 2996-3000.*

(Continued)

*Primary Examiner* — Krishnan S Menon
(74) *Attorney, Agent, or Firm* — Christensen, Fonder, Dardi & Herbert PLLC

(57) ABSTRACT

Novel block copolymers comprising at least one (poly)2-$C_{1-3}$alkyl-2-oxazoline block and at least one (poly)dimethyl siloxane block, having at least one end group X which includes both an —$NH_2$ group and an —NH— group, have been found to be particularly suitable for forming vesicles. The vesicles may be used to form filtration membranes.

20 Claims, 4 Drawing Sheets

(56) References Cited

U.S. PATENT DOCUMENTS

| | | | |
|---|---|---|---|
| 2008/0305149 A1* | 12/2008 | Hirt | A61K 9/0053 424/434 |
| 2009/0007555 A1 | 1/2009 | Jensen | |
| 2011/0046074 A1 | 2/2011 | Kumar et al. | |
| 2012/0043275 A1 | 2/2012 | Montemagno et al. | |
| 2012/0080377 A1 | 4/2012 | Jensen et al. | |
| 2014/0332468 A1 | 11/2014 | Tang et al. | |
| 2015/0136690 A1 | 5/2015 | Xie et al. | |

OTHER PUBLICATIONS

Duong, Phuoc H.H., et al., "Planar biomimetic aquaporin-incorporated triblock copolymer membranes on porous alumina supports for nanofiltration," *Journal of Membrane Science*, 409-410 (2012), pp. 34-43.

Egli, Stefan, et al., "Biocompatible Functionalization of Polymersome Surfaces: A New Approach to Surface Immobilization and Cell Targeting Using Polymersomes," *J. Am. Chem. Soc.*, 133, (2011), pp. 4476-4483.

Kumar, Manish, et al., "Highly permeable polymeric membranes based on the incorporation of the functional water channel protein Aquaporin Z,"*PNAS*, vol. 104, No. 52, (Dec. 26, 2007), pp. 20719-20724.

Tang, C.Y., et al., "Desalination by biomimetic aquaporin membranes: Review of status and prospects," *Desalination*, (2012), doi:10,1016/j.desal.2012.07.007.

Wang, Hong Lei, et al., "Mechanically robust and highly permeable AquaporinZ biomimetic membranes," *Journal of Membrane Science*, 434 (2013), pp. 130-136.

Xie, Wenyuan, et al., "An aquaporin-based vesicle-embedded polymeric membrane for low energy water filtration," *J. Mater. Chem. A*, 1 (2013), 9 pgs.

Zhao, Yang, et al. "Synthesis of robust and high-performance aquaporin-based biomimetic membranes by interfacial polymerization-membrane preparation and RO performance characterization," *Journal of Membrane Science*, 423-424 (2012), pp. 422-428.

Zhong, Pei Shan, et al. "Aquaporin-embedded biomimetic membranes for nanofiltration," *Journal of Membrane Science*, 407-408 (2012), pp. 27-33.

\* cited by examiner

Figure 7A
Figure 7B
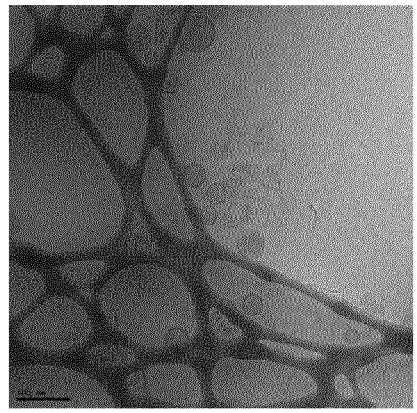
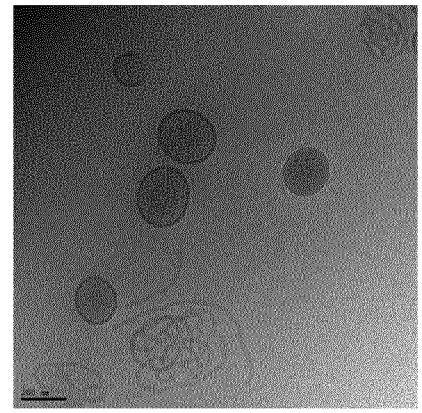
Figure 8A
Figure 8B
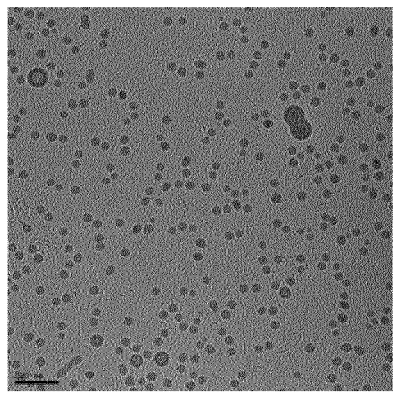
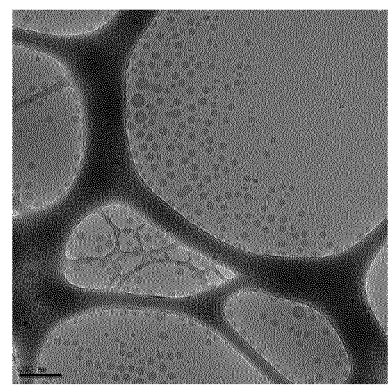

POLYMERS AND PROCESS FOR MAKING MEMBRANES

PRIORITY CLAIM

The present application is a National Phase entry of PCT Application No. PCT/EP2015/056294, filed Mar. 24, 2015, which claims priority from Great Britain Patent Application Number 1405391.2, filed Mar. 26, 2014, the disclosures of which are hereby incorporated by reference herein in their entirety.

FIELD OF THE INVENTION

The present invention relates to novel polymers and a process for making membranes. Specifically, it relates to novel (poly)2-$C_{1-3}$alkyl-2-oxazoline/(poly)dimethyl siloxane block copolymers and to processes for making filtration membranes, especially water filtration membranes.

BACKGROUND OF THE INVENTION

Conventional nanofiltration or reverse osmosis water filtration membranes have been known for many decades. Typically, they are made by casting a support membrane (often polysulfone or polyethersulfone); immersing the resulting cast in an aqueous solution of a diamine; removing excess from the surface of the membrane; immersing the membrane in an organic solution of a trifunctional acyl halide; and curing the resulting product to produce a polyamide layer. Washing and secondary coating are then carried out as necessary.

It is known from WO 01/32146 that membrane proteins may be incorporated into the walls of vesicles made from amphiphilic ABA block copolymers. This document includes extensive discussion of the nature of the polymers, and discloses that the polymers may have polymerizable groups at both chain ends. These polymerizable groups can be polymerized after the formation of the self-assembled vesicles, the polymerisation occurring exclusively intravesicularly. WO 2004/011600 discloses that aquaporins may be incorporated into triblock co-polymers to form a membrane which will only pass water, excluding all contaminants. Since these disclosures, much work has been carried out to develop commercially viable membranes incorporating transmembrane proteins, and particularly water filtration membranes based on aquaporins. The challenge is to produce a working membrane, which is physically sufficiently robust to withstand the necessary conditions. WO 2009/076174 describes a method of preparing substantially flat membranes based on block copolymers and aquaporins. According to Zhao et al, J. Membrane Sci. 2012, 422-428, various proposed methods of producing aquaporin membranes include polymer tethered bio-layers, biomembrane aperture partition arrays, membrane supported lipid bilayer via vesicle fusion, and vesicles suspended over membrane pores, but most of these are not able to withstand the high hydrostatic pressure that is required. Zhao's own solution to the problem is in effect to use a conventional membrane preparation as described above, modified by addition of aquaporin-loaded lipid vesicles (i.e. liposomes) to the aqueous solution of diamine. The result provides liposomes embedded in a polyamide layer. Although Zhao reports the results obtained positively, it is clear from the data provided that although a small increase of water flux is obtained (FIG. 4(a)) no enhancement of the ability of the membrane to reject solute is found compared with conventional membranes (FIG. 5). It is believed that this is because the aquaporin-loaded liposomes become completely surrounded by polyamide, and thus the primary water flux through the membrane is via the polyamide (i.e. via the conventional path of the base membrane), and only partially through the aquaporin channels. WO 2013/043118, also from Zhao et al, describes the same technology and also discloses that block copolymers can be used to form vesicles, either containing or not containing aquaporins, and embedded in a polyamide layer. Again, the results plainly show that water flux via the polyamide layer and not exclusively via the aquaporin channels is obtained.

Xie et al, J. Mater. Chem A, 2013, 1, 7592 describes a process comprising (i) incorporating aquaporin into self-assembled polymer vesicles based on a polymer primarily (95%) having methacrylate end groups but also containing some (3%) carboxylic acid end groups; (ii) cross-linking the methacrylate end groups using UV light; (iii) depositing and covalently immobilizing the cross-linked vesicles on a support in such a concentration that isolated vesicles are disposed separately from each other on the surface of the support; and (iv) creating a thin polymer layer between the individual vesicles by the process known as "surface imprinting". In this process, it is important that the size of the immobilized vesicles is such that they are larger than the thickness of the imprinted polymer layer to prevent blockage of the aquaporin water channels. The process is said to exhibit high mechanical strength and stability during water filtration, but it is also stated that the most critical issue is that the imprinted polymer layer was not sufficiently dense to prevent all of the solute and water molecules from permeating. Further, only very limited flow rates are obtainable by such a system.

Accordingly, there still remains a need for a process which leads to a physically robust membrane incorporating transmembrane proteins, particularly a membrane which uses aquaporins acting effectively for water filtration. Our copending application ref. no. P021889WO claiming priority from GB 1405390 relates to such a membrane: that invention provides a filtration membrane which comprises a porous support and, covalently bonded to a surface thereof, a layer comprising a plurality of vesicles having transmembrane proteins incorporated therein, said vesicles being formed from an amphiphilic block copolymer, characterised in that within said layer, vesicles are covalently linked together to form a coherent mass.

The propensity of known amphiphilic polymers to form vesicles, rather than other self-assembly structures such as miscelles, is known to depend on the absolute and relative sizes of the hydrophobic and hydrophilic blocks. Previously, the nature of these blocks has been believed to be much the most important factor determining the ease with which vesicles can be formed. Polymers with a number of different end groups have been used in vesicle formation, but no effect on vesicle formation has been noted. For example, US 2008/0305149 discloses PMOXA-PDMS-PMOXA block copolymers having —OH, —$NH_2$, —NH-piperazine, —SH and —COONa end groups. Surprisingly, we have now found that the presence of an end group including both —$NH_2$ and —NH— groups, i.e. which includes both primary and secondary amine groups, makes a major difference, and the use of (poly)2-$C_{1-3}$alkyl-2-oxazoline, especially (poly)2-methyl-2-oxazoline/(poly)dimethyl siloxane block copolymers having at least one such end group has proved particularly valuable for the preparation of vesicles.

SUMMARY OF THE INVENTION

The invention provides a block copolymer comprising at least one (poly)2-$C_{1-3}$alkyl-2-oxazoline block and at least one (poly)dimethyl siloxane block, having end groups which include both an —$NH_2$ and an —NH— group. The invention also provides a vesicle formed from such a block copolymer, such vesicles having transmembrane proteins incorporated therein, a filtration membrane comprising such protein-containing vesicles, and processes for making filtration membranes.

DETAILED DESCRIPTION OF THE INVENTION

The block copolymer of the invention comprises at least one (poly)2-$C_{1-3}$alkyl-2-oxazoline block and at least one (poly)dimethyl siloxane block, having at least one end group X which includes both an —$NH_2$ and an —NH— group. The polymer is suitably a diblock copolymer AB or, preferably, a triblock copolymer ABA, in which (poly)2-$C_{1-3}$alkyl-2-oxazoline forms the A blocks and (poly)dimethyl siloxane forms the B block. (Poly)2-$C_{1-3}$alkyl-2-oxazoline and especially (poly)2-methyl-2-oxazoline/(poly)dimethyl siloxane block copolymers are well known in the art.

The $C_{1-3}$alkyl group in the (poly)2-$C_{1-3}$alkyl-2-oxazoline block may be methyl, ethyl or propyl or a mixture thereof. Preferably the or each (poly)2-$C_{1-3}$alkyl-2-oxazoline block is a (poly)2-methyl-2-oxazoline block. Throughout this specification, unless the context requires otherwise, any mention of $C_{1-3}$alkyl should be understood to include a specific mention of methyl.

The mean molecular weight (g/mol) of a (poly)dimethyl siloxane block is preferably in the range from about 500 to about 50,000, preferably in the range from about 800 to about 15,000, more preferably in the range of about 1,000 to 12,000, particularly preferably in the range from about 5,000 to about 12,000.

The mean molecular weight (g/mol) of a (poly)2-$C_{1-3}$alkyl-2-oxazoline block is suitably in the range from about 200 to about 50,000, preferably in the range from about 800 to about 15,000, more preferably in the range of about 1,000 to 12,000, particularly preferably in the range from about 5,000 to about 12,000.

Synthesis of block copolymers by polymerisation is well known, and the length of the one or more segments which are to be copolymerized on the starting segment can be easily controlled by controlling the amount of monomer which is added for the copolymerization, and/or by the addition of suitable chain-terminating capping agents. In this way the size of the segments and their ratio can easily be controlled.

It is well known in the art that the absolute and relative lengths of the blocks are important in determining the suitability of the copolymers for forming vesicles (so called polymer hydrophobic ratio). Further, as the intended use of the polymers according to the invention is in the formation of vesicles having transmembrane proteins incorporated therein as discussed below, the length of the blocks is preferably such that the thickness of the vesicle wall is broadly comparable with the length of the transmembrane protein so that the protein can be readily incorporated into the vesicle walls without the channel becoming blocked. For example the thickness of the vesicle wall may be in the range of from 1 nm to 50 nm. The length of the hydrophobic (poly)dimethyl siloxane block is particularly important, and this should preferably be no greater than 150 repeat units.

An especially preferred block copolymer for use in the present invention is PAOXA-a-PDMS-b-PAOXA-a, preferably PMOXA-a-PDMS-b-PMOXA-a, in which PAOXA is (poly)2-$C_{1-3}$alkyl-2-oxazoline and PMOXA is (poly)2-methyl-2-oxazoline, and PDMS is (poly)dimethyl siloxane. Preferably each a independently is a number between 5 and 100, for example between 10 and 100, and b is a number between 5 and 150, for example between 20 and 150. Various PAOXA-PDMS-PAOXA polymers are commercially available, and others can be readily synthesised by known methods.

The key feature of the present invention is that the block copolymer contains at least one reactive end group X which contains both an —$NH_2$ and an —NH— group, i.e. the end group includes both a primary and a secondary amine group. This end group may be present following initial synthesis of the copolymer, or it may be introduced following the copolymer synthesis. If not present following initial synthesis, it is possible to introduce an appropriate reactive group by suitable reactions at the end of the relevant block. For this purpose, the polymerization of the growing segment may be terminated after a suitable chain length is reached and the initiator group present at the chain end capped. Capping using an appropriate amine will lead to the required polymer. Alternative, capping may be carried out using any other desired terminator, and the required amine group may be introduced using known chemistry. For example, termination may be carried out using KOH/EtOH or unsaturated groups at the end of the growing segment. Hydroxyl groups may also be introduced into the copolymers by employing suitable comonomers in the copolymerization, e.g. 2-hydroxy-alkyloxazolines. The end groups may then be reacted using conventional chemistry to introduce the required groups.

In a particularly preferred embodiment of the invention, the amphiphilic block copolymers are terminated by end groups X having the formula —NHR in which R represents an alkyl group which may be straight-chain or branched having from 1 to 6 carbon atoms substituted by at least one, for example 1, 2 or 3, —$NH_2$ groups. Preferably such an end group X has the formula —NH—CH—$(NH_2)_2$ or, preferably, —NH—$(CH_2)_n$—$NH_2$, in which n is an integer from 2 to 6, preferably 2 to 4, especially 2. Such end groups may be introduced by reacting a polymer having —OH end groups with a suitable reactive amine $NH_2R$, for example a diamine, for example $H_2N$—$(CH_2)_n$—$NH_2$, especially $H_2N$—$(CH_2)_2$—$NH_2$, or triamine, for example N.$([CH_2]_nNH_2)_3$ or CH.$([CH_2]_nNH_2)_3$, for example $CH(NH_2)_3$ or tris(3-aminopropyl)amine. Branched oligomeric imines may also be used. Alternatively, as mentioned above, the growing polymer chain can be capped using an appropriate amine.

As mentioned above, our copending application ref. no. P021889WO relates to a filtration membrane which comprises a porous support and, covalently bonded to a surface thereof, a layer comprising a plurality of vesicles having transmembrane proteins incorporated therein, said vesicles being formed from an amphiphilic block copolymer, characterised in that within said layer, vesicles are covalently linked together to form a coherent mass. The block copolymers of the present invention, and vesicles made from them, have particular utility in such membranes. In such membranes, in complete contrast to the process of Xie mentioned above, the support carries a layer of vesicles in which multiple vesicles are close packed together. The packing in the layer may for example be hexagonal close packing. The layer of vesicles present on the support surface is thicker than the average diameter of the vesicles, i.e. it is of greater thickness than would be provided by a single layer of vesicles. It is preferred that the layer should have a thickness equivalent to at least 2, for example at least 10, preferably at least 50, more preferably at least 150, and most preferably at least 200, times the average diameter of vesicles. Preferably the layer is not more than 500 times, for example not more than 300 times, the average diameter of a vesicle. So, for example, the layer may have a thickness of from 2 to 500, for example from 50 to 300, especially from 200 to 300 times the average diameter of the vesicles. In absolute terms, the thickness of the vesicle layer is preferably at least 0.04, for example at least 0.1, for example at least 0.2, for example at least 2, preferably at least 10, more preferably at least 30, and most preferably at least 40, microns. There is no particularly preferred maximum thickness for the layer. The layer may for example have a thickness up to 100, for example up to 60, microns. So, for example, the layer may have a thickness of from 0.04 to 100, for example from 0.2 to 100, preferably from 10 to 60, especially from 40 to 60, microns.

To increase robustness, the layer of vesicles in the finished membrane is preferably provided with a protective top coating layer, or a second support layer on the opposite side from the support layer. This top coating may for example provide added protection from mechanical damage during a rolling process. It may for example comprise a hydrophilic polymer, for example polyvinylalcohol.

A filtration membrane according to our copending application may be prepared by a process which comprises providing an aqueous suspension of vesicles having transmembrane proteins incorporated therein, said vesicles being formed from a block copolymer according to the present invention; depositing said suspension of vesicles on a surface of a porous support; and providing reaction conditions such that covalent bonds are formed between different vesicles and between vesicles and said surface.

Preferably, the filtration membrane is a water filtration membrane, and preferably the transmembrane protein is an aquaporin. Throughout this Specification and claims, unless the context requires otherwise, any reference to a filtration membrane should be understood to include a specific reference to a water filtration membrane, and any reference to a transmembrane protein should be understood to include a specific reference to an aquaporin.

The process for membrane preparation may be carried out in a number of different ways. In a first preferred embodiment, the process comprises:
(a) providing an aqueous suspension of vesicles having transmembrane proteins incorporated therein, said vesicles being formed from a block copolymer according to the invention;
(b) providing a multifunctional linking agent having at least two reactive groups Y which are reactive with polymer end groups X of said block copolymer;
(c) depositing said suspension of vesicles and said multifunctional linker on a support having a surface which is reactive with either polymer end groups X or reactive groups Y; and
(d) causing reaction of end groups X with groups Y, and either end groups X or groups Y with the surface of the support.

In a second preferred embodiment, a process comprises:
(a) providing a first aqueous suspension of vesicles having transmembrane proteins incorporated therein, said vesicles being formed from a block copolymer according to the invention;
(b) providing a second aqueous suspension of vesicles having transmembrane proteins incorporated therein, said vesicles being formed from a block copolymer having reactive end groups Y which are reactive with polymer end groups X of the block copolymers according to the invention;
(c) depositing said suspensions of vesicles on a support having a surface which is reactive with either polymer end groups X or Y; and
(d) causing reaction of end groups X with end groups Y, and either end groups X or end groups Y with the surface of the support.

The above processes result in a physically robust layer of polymer vesicles linked to each other, optionally via a linker, and also linked to the surface of the support.

One or both of the block copolymer end groups may be groups X which include both an $-NH_2$ and an $-NH-$ group. It is not necessary that all the block copolymer molecules used in the invention should have end groups containing both an $-NH_2$ and an $-NH-$ group. The proportion of block copolymer molecules having such end groups X is not critical, provided that there are sufficient such groups to react with reactive groups either in a second population of vesicles or in a multifunctional linker, to form a coherent mass. Generally, at least 10%, for example at least 20%, for example at least 30%, for example at least 40%, for example up to 60%, or up to 100%, of the block copolymer molecules used to form the vesicles will have functional end groups including both an $-NH_2$ and an $-NH-$ group. Similarly, it is not required that all end groups contain both an $-NH_2$ and an $-NH-$ group. It may for example be desired to use blends of block copolymers, one containing one reactive end group including both an $-NH_2$ and an $-NH-$ group, and the second containing a different reactive end group.

Suitable reactive groups Y which are capable of reacting with the end group including both an $-NH_2$ and an $-NH-$ group include activated carboxylic acid and/or azide, especially phenylazide, groups.

A wide variety of amine-based end groups including both an $-NH_2$ and a $-NH-$ group is available. It has been found that when providing amphiphilic block copolymers with such end groups, the ability of the block copolymer to self-assemble into vesicles is enhanced: this is surprising, as generally it is expected that the properties of amphiphilic block copolymers which most influence vesicle formation are (i) the size and nature of the blocks; and (ii) the polydispersity of the polymer.

When using a multifunctional linking agent, the reactive groups present in that agent may be the same as each other, or they may be different. They must be such as to react with the complementary reactive group present in the vesicles and/or with the surface of the support. Suitable groups are as mentioned above. When using a multifunctional reagent, the reagent may for example contain 3 or 4 reactive groups, but preferably it contains two reactive groups, and any reference herein to a multifunctional reagent should be understood to include a specific reference to a difunctional reagent.

When preparing membranes according to the invention, the surface of the support may be functionalised in one or more steps to introduce specific reactive groups Z capable of reacting with complementary reactive groups X (i.e. groups including both —NH$_2$ and —NH—) and/or Y. Suitable groups include amine groups (reactive with for example carboxylic acid or activated carboxylic acid groups X and/or Y); carboxylic acid or activated carboxylic acid groups, (reactive with for example amine groups X and/or Y); and "click chemistry" groups (for example azide or alkyne groups reactive with alkyne or azide groups X and/or Y). One example of a multi-step functionalization of a surface is hydrolysis of a polyacrylonitrile surface using acid, e.g. hydrochloric acid, to introduce surface carboxylic acid groups, which may subsequently be activated using 1-ethyl-3-(3-dimethylaminopropyl)carbodiimide (EDC) and N-Hy-droxysuccinimide (NHS) followed by conversion into alkyne groups, for example using propargylamine, or into azide groups, for example using amino-triethyleneglycol-azide. However, in another embodiment of the invention, it may not be necessary to functionalise the surface of the support, because X and/or Y may be reactive with groups already present in the material forming the support. For example, Y may be an azide group: such groups are highly reactive once activated using UV light, and are capable of reacting with C—H bonds present in many polymers present in support materials. Specifically, azide, especially phenylazide, groups are capable of covalently bonding with polysulfones, which as discussed below, are a preferred support material for use in the present invention.

Where reference is made to an activated carboxylic acid group, this should be understood to include any conventional activated carboxylic acid group, for example an activated ester such as an N-hydroxysuccinimide ester, or an acid halide. Such activation techniques are well known in the art. In a preferred embodiment, activated carboxylic acid end groups are produced by the reaction of a carboxylic acid group with EDC and NHS. This is a well-known technique often used in the world of protein conjugation and immobilization. The reaction of a carboxyl group with EDC and NHS results in formation of an amine reactive NHS ester.

When using a multifunctional linker, its exact nature is not crucial, provided that it is capable of reacting efficiently to cause linking of the vesicles together by reaction of the X and Y groups.

Suitable multifunctional linkers include homobifunctional crosslinkers, that is, crosslinkers with the same functionalities at both ends. Examples which are capable of binding to amine groups include:

(i) NHS esters. Typical esters include:
disuccinimidyl glutarate:

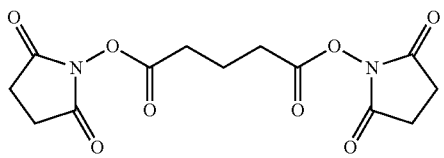 [SMILES: O=C(CCCC(=O)ON1C(=O)CCC1=O)ON1C(=O)CCC1=O]

bis(succinimidyl) polyethylene glycol:

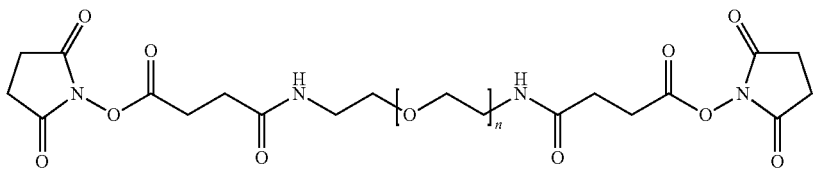

for example bis(succinimidyl penta(ethylene glycol);
ethylene glycol bis(sulfosuccinimidylsuccinate):

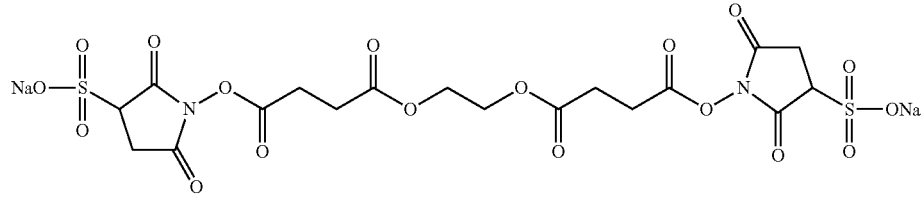

3,3'-dithiobis(sulfosuccinimidylpropionate):

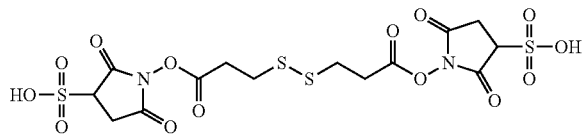 [SMILES: O=C(CCSSCCC(=O)ON1C(=O)CC(S(=O)(=O)O)C1=O)ON1C(=O)CC(S(=O)(=O)O)C1=O]

bis(sulfosuccinimidyl)suberate:

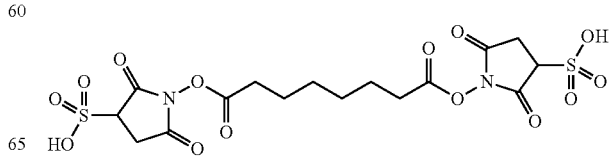

disuccinimidyl tartrate:

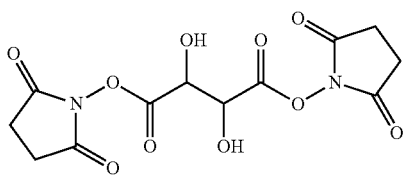 [SMILES: O=C(ON1C(=O)CCC1=O)C(O)C(O)C(=O)ON1C(=O)CCC1=O]

Reagents of this type react with primary amines in slightly alkaline conditions, for example at a pH of 7.2-8.5, for example 7.2-8.0, and yield stable amide bonds. Reaction temperatures are typically in the range of from 0 to 30, for example from 4 to 25° C. The reaction produces N-hydoxysuccinimide which can be removed via dialysis or desalting. The reaction may for example be carried out in PBS buffer at pH 7.2-8.0 for 0.5 to 4 hours at room temp or 4° C.

Sulfo NHS esters contain an —$SO_3$ group on the NHS ring. This has no effect on the chemistry of the reaction, but such reagents tend to have increased water solubility.

(ii) Imidoesters. Typical imidoesters include the following (often obtained as dihydrochloride salts):

dimethyl adipimidate:

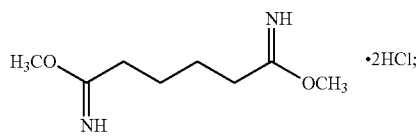 [SMILES: COC(=N)CCCCC(=N)OC]

dimethyl 3,3'-dithiobispropionimidate:

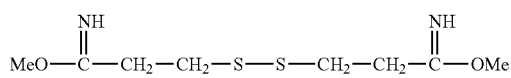

dimethyl suberimidate:

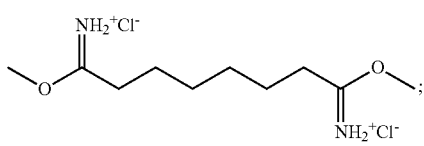

dimethyl pimelimidate:

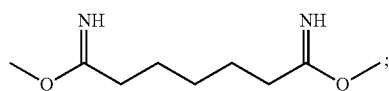

dimethyl adipimidate:

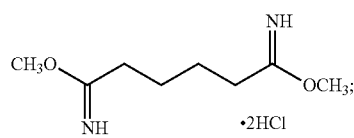

Imidoesters react with primary amines to form amidine bonds. To ensure specificity for primary amines, the reaction is typically carried out in amine-free alkaline conditions (pH 9-11, for example pH 10) with borate buffer.

(iii) genipin, which has the formula:

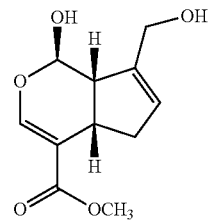 [SMILES: COC(=O)C1=CO[C@@H](O)[C@@H]2C(CO)=CC[C@H]12]

(iv) epoxides, for example triglycidylamine:

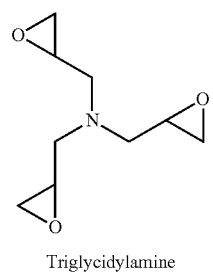 [SMILES: C1OC1CN(CC1CO1)CC1CO1]

Triglycidylamine (v) dialdehyde compounds, for example HOC.$(CH_2)_x$.CHO, where x is 1 to 6. Typical dialdehydes include glutaraldehyde, succindialdehyde, glyoxal, malondialdehyde, and phthalaldehyde.

(vi) COOH-PEG-COOH. This reagent is water-soluble, and if desired may be activated with EDC/NHS to provide reactivity with amines.

Suitable multifunctional linkers also include heterobifunctional crosslinkers, that is, crosslinkers with different functionalities at both ends. Examples include:

1-ethyl-3-(3-dimethylaminopropyl)carbodiimide (usually obtained in the form of the hydrochloride):

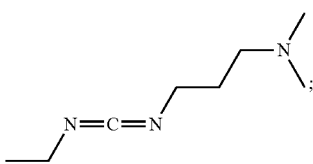

carbitol

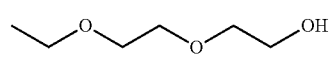

epoxides, for example triglycidalamine;
COOH-PEG-$NH_2$;
sulfosuccinimidyl 6-(4'-azido-2'-nitrophenylamino) hexanoate; poly(2-hydroxyethyl-co-2-methacryloxyethyl aspartamide); N,N'-disuccinimidyl carbonate:

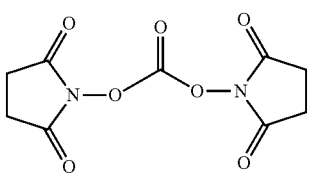 [SMILES: O=C(CON1C(=O)CCC1=O)ON1C(=O)CCC1=O]

p-azidobenzoyl hydrazide:

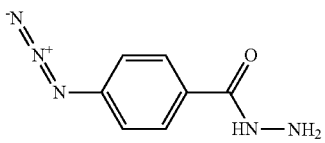

The process for membrane preparation may utilise "click chemistry", which may for example utilise the reaction of an azide with an alkyne. For example, an alkyne group may be introduced as a group Y by reaction of a primary amine with an NHS ester. Many azide-PEG-azide linkers are available commercially.

Preferably a multifunctional linker includes a $(CH_2)_m$ chain in which m is from 2 to 20, preferably from 3 to 10, especially from 3 to 9. An especially preferred difunctional linker is the commercially available product N-sulfosuccinimidyl-6-(4'-azido-2'-nitrophenylamino)hexanoate. This product has the formula:

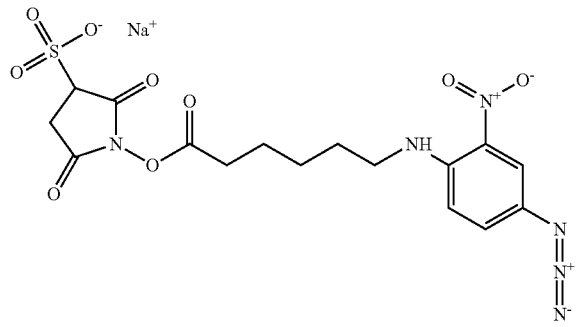 [SMILES: [N-]=[N+]=Nc1ccc(NCCCCCC(=O)ON2C(=O)CC(S(=O)(=O)[O-])C2=O)c([N+](=O)[O-])c1 ; [Na+]]

The sulfosuccinimide group is a reactive group Y which is an activated carboxylic acid ester, capable of reacting spontaneously with amine groups. The phenylazide group is a group Y which is inert under light-free conditions, but becomes highly reactive when activated using UV light, reacting readily with amine groups. In the absence of amine groups, the activated group is also capable of reacting with groups of a lower reactivity, even in some circumstances with a C—H bond; specifically, it is capable of reacting with the aromatic C—H groups in a polysulfone.

The conditions under which step (d) of the process for membrane preparation described above, i.e. causing reaction of complementary reactive groups X and Y, and reaction of either X or Y with the surface of the support, is carried out, will of course depend on the nature of the various reactive groups. In some embodiments, the reactive groups will react with each other spontaneously once contacted together under suitable conditions. In other embodiments, photo-activatable groups may be present, in which case the reactants may be contacted together, and subsequently photoirradiated to initiate reaction. In a preferred embodiment of the process of the invention, both mechanisms are combined by using a multifunctional reagent having a first group Y which reacts on contact with an end group X containing both an —NH₂ and an —NH— group, and a second group Y which reacts with an end group X and with the surface of the support on irradiation with UV light.

Thus, the steps of one embodiment of the process may be carried out as follows:

(a) providing an aqueous solution of vesicles having transmembrane proteins incorporated therein, said vesicles being formed from an amphiphilic block copolymer according to the invention having at least one reactive end group X including both an —NH₂ and an —NH— group;

(b) providing an multifunctional, preferably difunctional, linking agent having at least two reactive groups Y which are reactive with polymer end groups X, including a first reactive group Y(1) being capable of reaction with polymer end groups X under a first set of reaction conditions, and a second reactive group Y(2) which is unreactive with polymer end groups X under said first set of reaction conditions but which is reactive with polymer end groups X under a second set of reaction conditions;

(b') mixing said aqueous solution of vesicles with said multifunctional linking agent under said first set of reaction conditions so that reactive group Y(1) reacts with polymer end groups X;

(c) depositing the resulting solution on a support which is reactive with second reactive group Y(2), in an amount sufficient to produce the desired layer of vesicles; and (d) causing reaction of end groups X with said second reactive group Y(2), and second reactive end groups Y(2) with the surface of the support, by applying said second set of reaction conditions.

Any suitable reaction conditions which differentiate the two reaction steps may be used. For example, the first set of reaction conditions may involve groups X and Y(1) which react at a first temperature while the second set of reaction conditions may involve groups X and Y(2) which react at a second, higher, temperature. However, in a preferred embodiment, X and Y(1) are such that they react spontaneously on contact, or with heating if necessary, while X and Y(2) are such that they react only when activated by photoirradiation. Accordingly, a particularly preferred process comprises:

(a) providing an aqueous solution of vesicles having transmembrane proteins incorporated therein, said vesicles being formed from an amphiphilic block copolymer having at least one reactive end group X including both an —NH₂ and an —NH— group;

(b) providing an multifunctional, preferably difunctional, linking agent having at least two reactive groups Y which are reactive with polymer end groups X, including a first reactive group Y(1) being capable of reaction with polymer end groups X on contact, and a second reactive group Y(2) being capable of reaction with polymer end groups X on photoirradiation;

(b') mixing said aqueous solution of vesicles with said multifunctional linking agent under conditions such that said first reactive group Y(2) reacts with polymer end groups X;

(c) depositing the resulting solution on a support which is reactive with second reactive group Y(2), in an amount sufficient to produce the desired layer of vesicles; and (d) applying photoirradiation to cause reaction of end groups X with said second reactive group Y(2), and second reactive end groups Y(2) with the surface of the support.

In all the above embodiments, the amount of suspension deposited in step (c) is sufficient to provide the surface of the support with a continuous layer of vesicles. Generally, after step (d) has been carried out, this layer will be in the form of a coherent mass which has a thickness greater than the average diameter of the vesicles; or, in absolute terms, has a thickness of at least 0.01 microns, especially 0.04 microns.

A very wide range of reaction conditions may be used to effect the process of the invention. In one embodiment, when using a multifunctional linker, the quantity of multifunctional linker used will be such that the total quantity of reactive groups Y present is in excess of the total quantity of polymer end groups X present to ensure adequate crosslinking. Control of pH, temperature and other reaction conditions is conventional and within the normal practice of the skilled man.

Block copolymers can be prepared in the form of vesicles by methods well known in the art. Generally, these methods involve either solvent displacement or solvent-free rehydration. In solvent displacement methods, the block copolymer is dissolved in an organic solvent before mixing with water. After mixing, and optionally removing the organic solvent, spontaneous self-assembly of vesicles results. In solvent-free rehydration, dry block copolymer is brought into contact with an aqueous medium whereupon hydration results in the spontaneous self-assembly of vesicles. In a special case of solvent-free rehydration, the thin-film rehydration process, block copolymer is dissolved in an organic solvent which is then removed under conditions such that a thin film is formed. This film is then hydrated by contacting with water.

Vesicles having a desired size and low polydispersity can be obtained by known methods, for example by extrusion of large uni- and multi-lamellar polydisperse vesicles through one or more membranes of known pore size. Track etched polycarbonate membranes, for example Isopore (Trade Mark) membranes available from Millipore, are suitable for this purpose. Suitably, the vesicles used in the present invention have an average diameter in the range of from 30 to 10,000, preferably 50 to 1000, more preferably 100 to 400, especially from 150 to 250, nm.

The propensity of known PAOXA-a-PDMS-b-PAOXA-a polymers to form vesicles, rather than other self-assembly structures such as micelles, depends on the absolute and relative sizes of the blocks. Thus, when the polymer is terminated with —OH groups, as is known in the prior art, and when the blocks are relatively high molecular weight, for example as in $PAOXA_{14}PDMS_{55}PAOXA_{14}$ or higher, micelles tend to be formed, which means that lower molecular weight polymers need to be used if vesicles are required. Surprisingly, the presence of an end group including both an —NH$_2$ and an —NH— group makes a major difference, and the use of PAOXA-a-PDMS-b-PAOXA-a, for example $PAOXA_{14}PDMS_{55}PAOXA_{14}$ and in particular $PMOXA_{14}PDMS_{55}PMOXA_{14}$ having such end groups, for example:

$H_2N$—$(CH_2)_n$—NH-$PAOXA_{14}PDMS_{55}PAOXA_{14}$-NH—$(CH_2)_n$—$NH_2$ particularly $H_2N$—$(CH_2)_n$—NH-$PMOXA_{14}PDMS_{55}PMOXA_{14}$-NH—$(CH_2)_n$—$NH_2$ has proved particularly valuable for the preparation of vesicles.

Overall, the use of polymers according to the invention together with a complementary multifunctional linking agent gives major advantages compared with known processes for the preparation of working filtration membranes.

However the vesicles are formed, the vesicle formation process can be carried out in the presence of transmembrane proteins, especially aquaporins, whereby the transmembrane protein becomes incorporated into the wall of the vesicle. Generally, the process is carried out in the presence of a detergent which assists in maintaining the integrity and biological function of the protein. Thus, the above rehydration steps may be carried out using an aqueous solution of a transmembrane protein, preferably also including a detergent. The use of aquaporins is preferred, and aquaporins are robust under a wide range of process conditions.

Aquaporins are biological cell transmembrane proteins whose function is to selectively transport water and no other molecules; the transport channel of the protein is a two-way channel through which water can flow in either direction. They are expressed by many human cell types, and also by bacterial and plant cells. Any of the different members of the aquaporin family of proteins can be used in the present invention. Suitable aquaporins include Aqp 4, Aqp1 and, especially, Aqp Z. Aquaporins may exist in monomeric, dimeric, tetrameric and higher oligomeric forms, as well as mutated, conjugated and truncated versions of the primary sequence. Provided that the biological function of the aquaporin, i.e. the selective transport of water, is maintained, any of these may be used in membranes formed from block copolymers of the present invention.

Any other transmembrane protein having desirable transport properties may be used in the present invention. Variants of such transmembrane proteins, including naturally or non-naturally occurring variants and orthologs or paralogs of such proteins may be used. Such proteins include for example:

Monotopic Membrane Proteins
    Cyclooxygenases
        Ram Prostaglandin H2 synthase-1 (cyclooxygenase-1 or COX-1): *Ovis aries*
        Ram Prostaglandin H2 synthase-1 (COX-1) R120Q/Native Heterodimer: *Ovis aries*
        Aspirin Acetylated COX-1
        Cyclooxygenase-2: *Mus Musculus*
    Squalene-Hopene Cyclases
        Squalene-hopene cyclase: *Alicyclobacillus acidocaldarius*
    Monoamine Oxidases
        Monoamine Oxidase B: Human mitochondrial outer membrane
        Monoamine Oxidase A: Rat mitochondrial outer membrane
        Monoamine Oxidase A: Human mitochondrial outer membrane
        G110A mutant
    Hydrolases
        Fatty acid amide hydrolase: *Rattus norvegicus*
    Oxidoreductases (Monotopic)
        Sulfide:quinone oxidoreductase in complex with decylubiquinone: *Aquifex aeolicus*
        Electron Transfer Flavoprotein-ubiquinone oxidoreductase (ETF-QO): *Sus scrofa*
    Peptidoglycan Glycosyltransferases
        Peptidoglycan Glycosyltransferase: *Staphylococcus aureus*
        Peptidoglycan Glycosyltransferase penicillin-binding protein 1a (PBP1a): *Aquifex aeolicus*
        Peptidoglycan Glycosyltransferase penicillin-binding protein 1b (PBP1b): *Escherichia coli*
    Peptidases
        Signal Peptidase (SPase): *Escherichia coli*
        Signal Peptide Peptidase (SppA), native protein: *Escherichia coli*

Dehydrogenases
  Glycerol-3-phosphate dehydrogenase (GlpD, native): *Escherichia coli*
Dihydroorotate Dehydrogenases (DHODH, class 2)
  Dihydroorotate Dehydrogenase: *Escherichia coli*
  Dihydroorotate Dehydrogenase: *Rattus rattus*
  Dihydroorotate Dehydrogenase, apo form: *Homo sapiens*
  Dihydroorotate Dehydrogenase: *Plasmodium falciparum*: 3d7
Polymerases
  TagF teichoic acid polymerase: *Staphylococcus epidermidis*
ADP-Ribosylation Factors
  ADP-ribosylation factor (ARF1), myristoylated: *Saccharomyces cerevisiae*
  ADP-ribosylation factor (ARF1*GTP), myristoylated: *Saccharomyces cerevisiae*
Isomerases
  RPE65 visual cycle retinoid isomerase: *Bos Taurus*
Transmembrane Proteins: Beta-Barrel
  Beta-Barrel Membrane Proteins: Multimeric
    Porin: *Rhodobacter capsulatus*
    Porin: *Rhodopeudomonas blastica*
    OmpK36 osmoporin: *Klebsiella pneumonia*
    Omp32 anion-selective porin: *Comamonas acidovorans*
    Omp32 anion-selective porin: *Delftia acidovorans*
    OmpF Matrix Porin: *Escherichia coli*
    OmpC Osmoporin: *Escherichia coli*
    OmpG *monomeric* porin: *Escherichia coli*
    PhoE: *Escherichia coli*
    LamB Maltoporin: *Salmonella typhimurium*
    LamB Maltoporin: *Escherichia coli*
    LamB Maltoporin: *Escherichia coli*
    ScrY sucrose-specific porin: *Salmonella typhimurium*
    MspA mycobacterial porin: *Mycobacterium smegmatis*
    OprP phosphate-specific transporter: *Pseudomonas aeruginosa*
    OprD basic amino acid uptake channel: *Pseudomonas aeruginosa*
    OpdK hydrocarbon transporter: *Pseudomonas aeruginosa*
    PorB outer membrane protein, native structure: *Neisseria meningitidis*
  Beta-Barrel Membrane Proteins: Monomeric/Dimeric
    TolC outer membrane protein: *Escherichia coli*
    TolC outer membrane protein, ligand blocked: *Escherichia coli*
    TolC outer membrane protein (Y362F, R367E): *Escherichia coli*
      C2 Form
      P2:2:2 form
    VceC outer membrane protein: *Vibrio cholera*
    OprM drug discharge outer membrane protein: *Pseudomonas aeruginosa*
    CusC heavy metal discharge outer membrane protein: *Escherichia coli*
    CusBA heavy-metal efflux complex outer membrane protein: *Escherichia coli*
    BenF-like Porin (putative): *Pseudomonas fluorescens*
    OprM drug discharge outer membrane protein: *Pseudomonas aeruginosa*
    apo BtuB cobalamin transporter: *Escherichia coli*
    BtuB: *Escherichia coli*
    apo BtuB by in meso crystallization: *Escherichia coli*
    Colicin I receptor: *Escherichia coli*
    OmpA: *Escherichia coli*, 2.5 Å
    OmpA with four shortened loops: *Escherichia coli*
      Called β-barrel platform (BBP)
    OmpT outer membrane protease: *Escherichia coli*
    Pla Plasminogen activator (native 1): *Yersinia pestis*
    OmpW outer membrane protein: *Escherichia coli*
      Orthorhombic Form
      Trigonal Form
    OprG outer membrane protein: *Pseudomonas aeruginosa*
    OmpX: *Escherichia coli*
    TtoA Outer Membrane Protein (OMP): *Thermus thermophilus* HB27
    OmpLA (PldA) outer membrane phospholipase A monomer: *Escherichia coli*
    OmpLA (PldA) active-site mutant (N156A): *Escherichia coli*
    OpcA adhesin protein: *Neisseria meningitidis*
    NspA surface protein: *Neisseria meningitides*
    NalP autotransporter translocator domain: *Neisseria meningitides*
    NanC Porin, model for KdgM porin family: *Escherichia coli*
    Hia1022-1098 trimeric autotransporter: *Haemophilus influenza*
      Hia992-1098
    EspP autotransporter, postcleavage state: *Escherichia coli*
    EstA Autotransporter, full length: *Pseudomonas aeruginosa*
    PagP outer membrane palmitoyl transferase: *Escherichia coli*)
    FadL long-chain fatty acid transporter: *Escherichia coli*
    FadL long-chain fatty acid transporter A77E/S100R mutant: *Escherichia coli*
      ΔS3 kink
      P34A mutant
      N33A mutant
      ΔNPA mutant
      G212E mutant
    FadL homologue long-chain fatty acid transporter: *Pseudomonas aeruginosa*
    FauA alcaligin outer membrane transporter: *Bordetella pertussis*
    TodX hydrocarbon transporter: *Pseudomonas putida*
    TbuX hydrocarbon transporter: *Ralstonia pickettii*
    Tsx nucleoside transporter (apoprotein): *Escherichia coli*
    FhuA, Ferrichrome-iron receptor: *Escherichia coli*
    FepA, Ferric enterobactin receptor: *Escherichia coli*
    FecA, siderophore transporter: *Escherichia coli*
    HasR heme-uptake receptor: *Serratia marcescens*
      Ile671Gly mutant
    FptA, pyochelin outer membrane receptor: *Pseudomonas aeruginosa*
    FpvA, Pyoverdine receptor: *Pseudomonas aeruginosa*
    FpvA, Pyoverdine receptor (apo form): *Pseudomonas aeruginosa*
    P pilus usher translocation domain, PapC130-640: *Escherichia coli*

Beta-Barrel Membrane Proteins: Mitochondrial Outer Membrane
　VDAC-1 voltage dependent anion channel: *Human*
　VDAC-1 voltage dependent anion channel: *Murine*
Omp85-TpsB Outer Membrane Transporter Superfamily
　FhaC Filamentous Hemagglutinin Transporter: *Bordetella pertussis*
　TeOmp85-N POTRA domains: *Thermosynechococcus* anaOmp85-N *Anabaena* sp. PCC7120
　BamA: *Escherichia coli*
　BamE: *Escherichia coli*
Non-constitutive. Beta-sheet Pore-forming Toxins
　Alpha-hemolysin: *Staphylococcus aureus*
　LukF: *Staphylococcus aureus*
　Perfringolysin O (PFO) protomer: *Clostridium perfringens*
　Anthrax Protective Antigen (PA) and Lethal Factor (LF) Prechannel Complex: *Bacillus anthraciss*
　Lymphocyte preforin monomer: *Mus musculus*
Transmembrane Proteins: Alpha-Helical
　Non-constitutive. Alpha-helical Pore-forming Toxins.
　　Cytolysin A (ClyA, aka HlyE): *Escherichia coli*
　　FraC eukaryotic pore-forming toxin from sea anemone: *Actinia fragacea*
　Outer Membrane Proteins
　　Wza translocon for capsular polysaccharides: *Escherichia coli*
　　Porin B monomer: *Corynebacterium glutamicum*
　　Type IV outer membrane secretion complex: *Escherichia coli*
　　Bacteriorhodopsin (BR): *Halobacterium salinarium*
　　Halorhodopsin (HR): *Halobacterium salinarium*
　　Halorhodopsin (HR): *Natronomonas pharaonis*
　　Sensory Rhodopsin I (SRI): *Anabaena (Nostoc)* sp. PCC7120
　　Sensory Rhodopsin II (SRII): *Natronomonas pharaonis*
　　Archaerhodopsin-1 (aR-1): *Halorubrum* sp. aus-1
　　Archaerhodopsin-2 (aR-2): *Haloroubrum* sp. aus-2
　　Xanthorhodopsin: *Salinibacter ruber*
　G Protein-Coupled Receptors (GPCRs)
　　Rhodopsin: Bovine Rod Outer Segment (*Bos Taurus*)
　　Rhodopsin: Squid (*Todarodes pacificus*)
　　β1 adrenergic receptor (engineered): *Meleagris gallopavo* (turkey)
　　β2 adrenergic receptor: *Homo sapiens*
　　Methylated β2 adrenergic receptor: *Homo sapiens*
　　A2A adenosine receptor: *Homo sapiens*
　　CXCR4 Chemokine Receptor: *Homo sapiens*
　　Dopamine D3 Receptor: *Homo sapiens*
　Autonomously Folding "Membrane Proteins" (Sec-independent)
　　Mistic membrane-integrating protein: *Bacillus subtilis*
　Glycoproteins
　　Glycophorin A transmembrane-domain dimer: *Homo sapiens*
　SNARE Protein Family
　　Syntaxin 1A/SNAP-25/Synaptobrevin-2 Complex: *ratus ratus*
　Integrin Adhesion Receptors
　　Human Integrin αIIbβ3 transmembrane-cytoplasmic heterodimer: *Homo sapiens*
　Histidine Kinase Receptors
　　ArcB (1-115) Aerobic Respiration Control sensor membrane domain: *Escherichia coli*
　　QseC (1-185) Sensor protein membrane domain: *Escherichia coli*
　　KdpD (397-502) Sensor protein membrane domain: *Escherichia coli*
　Immune Receptors
　　Transmembrane ζ-ζ dimer of the TCR-CD3 complex: *Homo sapiens*
　　DAP12 dimeric: *Homo sapiens*
　Channels: Potassium and Sodium Ion-Selective
　　KcsA Potassium channel, H+ gated: *Streptomyces lividans*
　　KcsA Potassium channel E71H-F103A inactivated-state mutant (closed state): *Streptomyces lividans*
　　KcsA Potassium channel E71I modal-gating mutant: *Streptomyces lividans*
　　KvAP Voltage-gated potassium Channel: *Aeropyrum pernix*
　　Kv1.2 Voltage-gated potassium Channel: *Rattus norvegicus*
　　Kv1.2/Kv2.1 Voltage-gated potassium channel chimera: *Rattus norvegicus*
　　F233W Mutant
　　MthK Potassium channel, Ca++ gated: *Methanothermobacter thermautotrophicus*
　　Human BK Channel Ca2+-activation apparatus: *Homo sapiens*
　　Kir3.1-Prokaryotic Kir Chimera: *Mus musculus & Burkholderia xenovornas*
　　Kir2.2 Inward-Rectifier Potassium Channel: *Gallus gallus*
　　KirBac1.1 Inward-Rectifier Potassium channel: *Burkholderia pseudomallei*
　　MlotiK1 cyclic nucleotide-regulated K+-channel: *Mesorhizobium loti*
　　mGIRK1 G-Protein Gated Inward Rectifying Potassium Channel: *Mus musculus*
　　NaK channel (Na+ complex): *Bacillus cereus*
　　　D66/S70E Mutant
　　　D66N Mutant
　　　D66E Mutant
　　CNG-mimicking NaK channel mutant: *Bacillus cereus*
　　NaK channel; K+ selective mutant: *Bacillus cereus*
　Channels: Other Ion Channels
　　GluA2 Glutamate receptor (AMPA-subtype): *Rattus norvegicus*
　　M2 proton channel: Influenza A
　　M2 proton channel: Influenza B
　　ASIC1 Acid-Sensing Ion Channel: *Gallus gallus*
　　ATP-gated P2X4 ion channel (apo protein): *Danio rerio* (zebra fish)
　　Nicotinic Acetylcholine Receptor Pore: *Torpedo marmorata*
　　Prokaryotic pentameric ligand-gated ion channel (pLGIC): *Erwinia chrysanthemi*
　　Prokaryotic pentameric ligand-gated ion channel (GLIC): *Gloebacter violaceus*
　　　E221A mutant
　　Prokaryotic pentameric ligand-gated ion channel (GLIC), wildtype-TBSb complex: *Gloebacter violaceus*
　　　Wildtype-TEAs complex
　　　E221D-TEAs complex
　　　Wildtype-TMAs complex
　　　Wildtype-bromo-lidocaine complex Wildtype-Cd2+ complex
Wildtype-Zn2+ complex
Wildtype-Cs+ complex
MscL Mechanosensitive channel: *Mycobacterium tuberculosis*
MscS voltage-modulated mechanosensitive channel: *Escherichia coli*
CorA Mg2+ Transporter: *Thermotoga maritime*
MgtE Mg2+ Transporter: *Thermus thermophilus*
SLAC1 anion channel, TehA homolog (wild-type): *Haemophilus influenzae*
  F262A mutant
  F262L mutant
  F262V mutant
  G15D mutant
Channels: Protein-Conducting
  SecYEβ protein-conducting channel: *Methanococcus jannaschii*
Channels: Aquaporins and Glyceroporins
  AQP0 aquaporin water channel: Bovine lens
  AQP1 aquaporin water channel: Human red blood cell
  AQP1 aquaporin water channel: Bovine red blood cell
  AQP4 aquaporin water channel: rat glial cells
    S180D Mutant
  AQP4 aquaporin water channel: Human
  AQP5 aquaporin water channel (HsAQP5): human
  AqpM aquaporin water channel: *Methanothermobacter marburgensis*
  AqpZ aquaporin water channel: *Escherichia coli*
  AqpZ aquaporin (C9S/C20S), T183C mutant: *Escherichia coli*
    L170C Mutant
  AqpZ aquaporin mutant F43W: *Escherichia coli*
    H17G/T183F Mutant
    F43WH174G/T183F Mutant
  SoPIP2;1 plant aquaporin: *Spinacia oleracea*
  GlpF glycerol facilitator channel: *Escherichia coli*
  GlpF glycerol facilitator channel, W84F/F200T-mutant: *Escherichia coli*
  PfAQP aquaglyceroporin: *Plasmodium falciparum*:
  Aqy1 yeast aquaporin (pH 3.5): *Pischia pastoris*
Channels: Formate Nitrate Transporter (FNT) Family
  FocA, pentameric aquaporin-like formate transporter: *Escherichia coli*
  FocA formate transporter without formate: *Vibrio cholerae*
  FocA formate transporter: *Salmonella typhimurium*
Channels: Urea Transporters
  Urea transporter: *Desulfovibrio vulgaris*
  Connexin 26 (Cx26; GJB2) gap junction: *Human*
Channels: Amt/Rh proteins
  AmtB ammonia channel (mutant): *Escherichia coli*
  AmtB ammonia channel (wild-type): *Escherichia coli*
    H168E Mutant
    H168A Mutant
    H168F Mutant
    H318A Mutant
    H318 Mutant
    H318F Mutant
    H168A/H318A Mutant
  Amt-1 ammonium channel: *Archaeoglobus fulgidus*
  Rh protein, possible ammonia or CO2 channel: *Nitrosomonas europaea*
  Human Rh C glycoprotein ammonia transporter: *Homo sapiens*
Intramembrane Proteases
  GlpG rhomboid-family intramembrane protease: *Escherichia coli*
    W136A Mutant
    S201T Active-Site Mutant
  GlpG rhomboid-family intramembrane peptidase: *Haemophilus influenzae*
  Site-2 Protease (S2P). Intramembrane Metalloprotease: *Methanocaldococcus jannaschii*
  Signal Peptide Peptidase (SppA), native protein: *Escherichia coli*
Membrane-Bound Metalloproteases
  apo-FtsH ATP-dependent metalloprotease: *Thermotoga maritima*
H+/Cl− Exchange Transporters
  H+/Cl− Exchange Transporter: *Salmonella typhimurium*
  H+/Cl− Exchange Transporter: *Escherichia coli*
    E148A Mutant
    E148Q Mutant
    S107A/E148Q/445A Mutant
  Monomeric H+/Cl− Exchange Transporter: *Escherichia coli*
  +/Cl− Eukaryotic Exchange Transporter: *Cyanidioschyzon merolae*
  H+/Cl− Eukaryotic Exchange Transporter: *Synechocystis* sp. pcc 6803
Bacterial Mercury Detoxification Proteins
  MerF Hg(II) transporter: *Morganella morganii*
Multi-Drug Efflux Transporters
  AcrB bacterial multi-drug efflux transporter: *Escherichia coli*
  AcrB bacterial multi-drug efflux transporter, apo protein, N109A mutant: *Escherichia coli*
  AcrB bacterial multi-drug efflux transporter, D407A mutant: *Escherichia coli*
  MexB bacterial multi-drug efflux transporter: *Pseudomonas aeruginosa*
  CusA metal-ion efflux pump: *Escherichia coli*
  EmrE bacterial multi-drug efflux transporter: *Escherichia coli*
  NorM Multidrug and Toxin Compound Extrusion (MATE) transporter (apo form): *Vibrio cholerae*
Membrane-Associated Proteins in Eicosanoid and Glutathione Metabolism (MAPEG)
  Microsomal Prostaglandin E Synthase 1: *Human*
  5-Lipoxygenase-Activating Protein (FLAP) with Bound MK-591 Inhibitor: *Human*
  Leukotriene LTC4 Synthase: *Human*
Major Facilitator Superfamily (MFS) Transporters
  LacY Lactose Permease Transporter (C154G mutant): *Escherichia coli*
  LacY Lactose Permease (wild-type) with TDG: *Escherichia coli*
  FucP Fucose Transporter in outward-facing conformation: *Escherichia coli*
    N162A Mutant
  GlpT Glycerol-3-Phosphate Transporter: *Escherichia coli*
  EmrD Multidrug Transporter: *Escherichia coli*
  PepTSo Oligopeptide-proton symporter: *Shewanella oneidensis*

Solute Sodium Symporter (SSS) Family
   vSGLT Sodium Galactose Transporter: *Vibrio parahaemolyticus*
      K294A Mutant
Nucleobase-Cation-Symport-1 (NCS1) Family
   Mhp1 Benzyl-hydantoin transporter: *Microbacterium liquefaciens*
Betaine/Choline/Carnitine Transporter (BCCT) Family
   BetP glycine betaine transporter: *Corynebacterium glutamicum*
   CaiT carnitine transporter: *Escherichia coli*
   CaiT carnitine transporter: *Proteus mirabilis*
Amino Acid/Polyamine/Organocation (APC) Superfamily
   AdiC Arginine:Agmatine Antiporter: *Escherichia coli*
      N22A, L123W Mutant
      N101A Mutant
   apo ApcT Na+-independent Amino Acid Transporter: *Methanocaldococcus jannaschii*
Amino Acid Secondary Transporters
   LeuTAa Leucine transporter: *Aquifex aeolicus*
   Wild-type LeuT transporter: *Aquifex aeolicus*
      E290S Mutant
   Mutant LeuT transporter with Nitroxide Spin Label (F177R1): *Aquifex aeolicus*
      I204R1 Mutant
   Glutamate Transporter Homologue (GltPh): *Pyrococcus horikoshii*
   Aspartate Transporter Li+-Bound State (GltPh): *Pyrococcus horikoshii*
Cation Diffusion Facilitator (CDF) Family
   YiiP Zinc Transporter: *Escherichia coli*
Antiporters
   NhaA Na+/H+ antiporter: *Escherichia coli*
   Mitochondrial ADP/ATP Carrier: Bovine heart mitochondria
Energy-Coupling Factor (ECF) Transporters
   RibU, S Component of the Riboflavin Transporter: *Staphylococcus aureus*
ATP Binding Cassette (ABC) Transporters
   BtuCD Vitamin B12 Transporter: *Escherichia coli*
   Sav1866 Multidrug Transporter: *Staphylococcus aureus*
   Molybdate Transporter ModB2C2: *Archaeoglobus fulgidus*
   ModBC Molybdate ABC Transporter: *Methanosarcina acetivorans*
   HI1470/1 Putative Metal-Chelate-type ABC Transporter: *Haemophilus influenza*
   MsbA Lipid "flippase" with bound AMPPNP: *Salmonella typhimurium*
   P-Glycoprotein: *Mus musculus* (mouse)
   MalFGK2-MBP Maltose uptake transporter complex: *Escherichia coli*
   MetNI Methionine uptake transporter complex: *Escherichia coli*
   FbpC ferric iron-uptake transporter nucleotide-binding domain: *Neisseria gonorrhoeae*
Superfamily of K+ Transporters (SKT proteins)
   TrkH potassium ion transporter: *Vibrio parahaemolyticus*
   Calcium ATPase: Rabbit sarcoplasmic reticulum
   Na,K-ATPase: Pig Kidney
   Na,K-ATPase: Shark
   Na,K-ATPase Regulatory Protein FXYD1: *Human*
   Phospholamban homopentamer: Human sarcoplasmic reticulum
   Plasma Membrane H+-ATPase: *Arabidopsis thaliana*
V-type ATPase
   Rotor of V-type Na+-ATPase: *Enterococcus hirae*
   V1-ATPase Complex: *Thermus thermophiles*
   A3B3 complex of V1-ATPase: *Thermus thermophilus*
F-type ATPase
   F1-ATPase from bovine heart mitochondria: *Bos Taurus*
   ATP synthase (Flc10): *S. cerevisiae*
   F1 ATPase: *S. cerevisiae*
   Rotor (c11) of Na+-dependent F-ATP Synthase: *Ilyobacter tartaricus*
   Rotor (c14) of H+-dependent F-ATP Synthase of spinach chloroplasts: *Spinacia oleracea*
   Rotor (c15) of H+-dependent F-ATP Synthase of an alkaliphilic cyanobacterium: *Spirulina platensis*
   Rotor (c13) of H+-dependent F-ATP Synthase: *Bacillus pseudofirmus*
   Peripheral stalk of H+-dependent F-ATP Synthase: *Thermus thermophilus*
Phosphotransferases
   Diacylglycerol kinase (DAGK): *Escherichia coli*
Hydrolases
   Estrone Sulfatase: *Human placenta*
Oxygenases
   Particulate methane monooxgenase (pMMO): *Methylococcus capsulatus*
   Particulate methane monooxgenase (pMMO): *Methylosinus trichosporium* OB3b
Oxidoreductases
   Sulfide:quinone oxidoreductase: *Aquifex aeolicus*
   Electron Transfer Flavoprotein-ubiquinone oxidoreductase (ETF-QO): *Sus scrofa*
   Glycerol-3-phosphate dehydrogenase (GlpD, native): *Escherichia coli*
   NarGHI Nitrate Reductase A: *Escherichia coli*
      K86A Mutant
      H66Y Mutant
   NrfH Cytochrome C Quinol Dehydrogenase: *Desulfovibrio vulgaris*
   DsbB-DsbA Periplasmic Oxidase Complex: *E. coli*
   DsbB-Fab complex: *Escherichia coli*
   wtDsbB-DsbA(Cys133A)-Q8 Complex: *E. coli*
   Vitamin K epoxide reductase: *Synechococcus* sp.
Mo/W bis-MGD Oxidoreductases
   Polysulfide Reductase PsrABC (native): *Thermus thermophiles*
Electron Transport Chain Complexes: Complex I
   Complex I membrane domain: *Escherichia coli*
   Complex I complete: *Thermus thermophiles*
Electron Transport Chain Complexes: Complex II
   Native Fumarate Reductase Complex: *Escherichia coli*
   Fumarate Reductase Complex: *Wolinella succinogenes*
   Formate dehydrogenase-N: *Escherichia coli*
   Succinate dehydrogenase (Complex II): *Escherichia coli*
   Succinate:ubiquinone oxidoreductase (SQR, Complex II): porcine heart mitochondria
   Succinate:ubiquinone oxidoreductase (SQR, Complex II): chicken heart mitochondria Electron Transport Chain Complexes: Complex III (Cytochrome bc1)
  Cytochrome bc1: *Bos Taurus*
  Cytochrome bc1: *Gallus gallus*
  Cytochrome bc1: *Sarcomyces cerevisiae*
  Cytochrome bc1: *Rhodobacter Sphaeroides*
Electron Transport Chain Complexes: Cytochrome b6f of Oxygenic Photosynthesis
  Cytochrome b6f complex: *Mastigocladus laminosus*
  Cytochrome b6f complex: *Chlamydomonas reinhardtii*
  Cytochrome b6f complex: *Nostoc* sp. PCC 7120
Electron Transport Chain Complexes: Complex IV (Cytochrome C Oxidase)
  Cytochrome C Oxidase, aa3: *Bos taurus* (bovine) heart mitochondria
  Cytochrome C Oxidase, aa3: *Paracoccus denitrificans* N131D Variant
  Cytochrome Oxidase, cbb3: *Pseudomonas stutzeri*
  Cytochrome ba3: *Thermus thermophilus*
  Cytochrome C Oxidase wild-type: *Rhodobacter sphaeroides*
  Ubiquinol Oxidase, cytochrome bo3: *E. coli*
Nitric Oxide Reductases
  Nitric Oxide Reductase: *Pseudomonas aeruginosa*
Photosystems
  Photosystem I: *Thermosynechococcus elongates*
  Photosystem I (plant): *Psium sativum*
  Photosystem II: *Thermosynechococcus elongates*
  Photosystem II: *Thermocynechococcus vulcanus*
Light-Harvesting Complexes
  Light-Harvesting Complex: *Rhodopseudomonas acidophila*
  Light-Harvesting Complex: *Rhodospirillum molischianum*
  Light-Harvesting Complex LHC-II, Spinach Photosystem II: *Spinacia oleracia*
  Light-Harvesting Complex CP29, Spinach Photosystem II: *Spinacia oleracia*
  Light-Harvesting Complex LHC-II, Pea Photosystem II: *Pisum sativum*
Photosynthetic Reaction Centers
  Photosynthetic Reaction Center: *Blastochloris viridis*
  Photosynthetic Reaction Center: *Rhodobacter sphaeroides*
  Photosynthetic Reaction Center: *Thermochromatium tepidum*

The support may be made of any suitable microporous material. It may for example be based upon a conventional membrane support, as used in reverse osmosis or ultrafiltration membranes. Such supports may for example be made from a polyolefin, cellulose, regenerated cellulose, cellulose acetate, polyacrylonitrile, polyethersulfone, or polysulfone. In a preferred embodiment of the invention, the support is made from a polysulfone.

Chemical functionality of the support membrane may be delivered in the form of additives, which may be either low molecular weight or polymeric, to the casting dope, or functionalization of the support surface, for example by chemical treatments, graft polymerisation or plasma polymerization. By these means, the following chemical transformations of the support may for example be accomplished: conversion of amine groups into carboxylic acid groups, or vice versa; conversion of aldehydes into amines; and conversion of hydroxyl groups into carboxylic acid groups. All such reactions are well known in the art.

Porous ultrafiltration membranes may for example be prepared by air casting, where the dissolved polymer solution passes under a series of air flow ducts that control the evaporation of the solvents in a very slow manner, solvent or emersion casting, where the dissolved polymer is spread onto a moving belt and run through a bath of liquid, and the liquid in the bath exchanges with the solvent in the lacquer and causes the formation of the pores; thermal casting, where heat is used to drive the solubility of the polymer in a given solvent system. The lacquer is then cast out onto a moving belt that is being cooled. Quenching the heat in the lacquer causes precipitation to start and the pores to form. Materials typically used in the process include but are not limited to cellulose regenerated, cellulose nitrate, cellulose acetate, polyamide, polysulfone, poly(ether sulfone), polycarbonate, poly(ether imide), poly(2,6-dimethyl-1,4-phenylene oxide), polyimide, poly(vinylidene fluoride), polytetrafluoroethylene, polypropylene, polyacrylonitrile, poly(methyl methacrylate, polyvinyl alcohol, and polydimethylsiloxane. The morphology of the cast is regulated by the configuration of the final module. It may for example comprise a flat-sheet for spiral wound elements; hollow-fibre for hollow-fibre elements; or it may be tubular.

Preparation of a membrane having a layer comprising a coherent mass of vesicles, said layer having a defined thickness, may be achieved by control of the concentration of vesicles present in the solution of vesicles applied to the support and/or by the volume of solution deposited on the support.

Xie et al, J. Mater. Chem A, 2013, 1, 7592, discloses processes involving crosslinking during the preparation of the polymer vesicles, but this crosslinking, which did not change the structure or dimension of the polymer vesicles (col. 2 p. 7596 top paragraph) is always internal crosslinking between the crosslinkable end groups corresponding to the groups X of the present invention. Similarly, the crosslinking disclosed in WO 01/32146 is always internal crosslinking. It is of course possible, depending on the nature of the various groups present, for internal cross-linking to occur in the vesicles of the present invention, but it is an essential feature of membranes made using block copolymers of the present invention that external crosslinking, preferably via a multifunctional linker, also takes place. The advantage of the present invention over the methods disclosed by Xie et al, and by Zhao et al, J. Membrane Sci. 2012, 422-428 and WO 2013/043118, is that any possible pathway through the membrane other than through the transmembrane proteins embedded in the walls of the polymer vesicles, is minimised, while providing a large number of possible transmembrane proteins per unit surface area of the support membrane, thus maximising flux through the membrane. The process is technically simple, and the resulting membranes are physically robust. Membranes prepared using the novel polymers of the present invention are particularly preferred, because of the ease with which such polymers can be formed into vesicles.

A further use for vesicles according to the invention is in the delivery of substances, particularly drugs. A wide variety of substances can be contained in the cavity of the vesicles defined by the wall of the vesicle by a number of different routes, for example by adding the substance to the block copolymer during its preparation, by introducing the substance to the block copolymer during vesicle formation, or by treating the vesicles with a solution of the substance until the substance has been absorbed into the vesicles. Amongst substances which may be considered are cosmetic agents, fragrances, dyes, pigments, photoactive compounds, metal particles, nanoparticles, biological polymers, biological organelles, cell organelles, and chemical reagents. Especially preferred is the use of vesicles in the field of drug delivery, and the invention further provides a vesicle according to the invention containing a drug, specifically containing a drug within the cavity defined by the vesicle wall. A wide variety of drugs may be used, for example small molecule drugs, toxins, cytoxic drugs, genes or RNA, and proteins, for example therapeutic proteins or enzymes.

BRIEF DESCRIPTION OF THE FIGURES

FIGS. 7A and 7B show scanning electron microscopy images of vesicles formed from the amine-terminated polymer of step b of Example 1, the scale bar of FIG. 7A being 500 and the scale bar of FIG. 7B being 200.
FIGS. 8A and 8B show scanning electron microscopy images of vesicles formed from the hydroxyl-terminated polymer analogous to the amine-terminated polymer prepared in step b of Example 1, the scale bar of FIG. 8A being 500 and the scale bar of FIG. 8B being 200.

The following Examples illustrate the invention.

EXAMPLE 1

Materials

| Item | Supplier | Prod. # |
| --- | --- | --- |
| 2-Methyl-2-Oxazoline | Sigma | 137448 |
| Triethylamine | Sigma | 471283 |
| Hexane, Anhydrous | Sigma | 296090 |
| Ethylene Diamine | Sigma | 391085 |
| Trifluoromethanesulfonic Acid | Sigma | 176176 |
| Ethyl Acetate | Sigma | 270989 |
| Syringe gas tight | Hamilton | 100 ml |
| Reflux condenser | | |
| Three-neck flask | | 500 ml |
| Dry argon | | |
| Vacuum pump | Vacubrand | RC6 |
| Rubber septa | | |
| Ethanol | Sigma | |

Step a). α,ω-Hydroxy-butyl-poly-di-methyl-siloxane (PDMS) Synthesis

Targeting the molecular weight of 4000 g/mol, 93.03 g (0.34 mols) of octamethylcyclotetrasiloxane and 6.97 g (0.0025 mols) 1,3-bis(hydroxybutyl)-tetramethyldisiloxane were charged into a 3-necked round bottom Pyrex reactor with an argon inlet, thermometer and condenser. Trifluoroacetic acid 6.55 g (0.05755 mols) was added. The reaction mixture was heated at 60° C. for 48 hours. After this time the excess trifluoroacetic acid was extracted with distilled water until the aqueous extract was neutral. Then the reaction mixture was stripped off under high vacuum to remove the cyclic side products. Ester groups were further converted to alcohols by a weak base catalyzed hydrolysis in THF and an equal volume of 5% aqueous sodium carbonate solution at 40-45° C., for 48 hours. Organic and aqueous phases were separated out. The 83.72 grams of product were recovered by the evaporation of THF. The product was evaluated for molecular weight by proton NMR and molecular weight distribution by GPC in chloroform.

Step b). Primary/Secondary-Amine Terminated poly-2-methyloxazoline-poly-di-methyl-siloxane-poly-2-methyloxazoline (PMOXA-PDMS-PMOXA) Synthesis Hydroxyl-terminated PDMS synthesized as in step a above was used in the synthesis of poly PMOXA-PDMS-PMOXA amphiphilic block copolymer.

Figure 1:
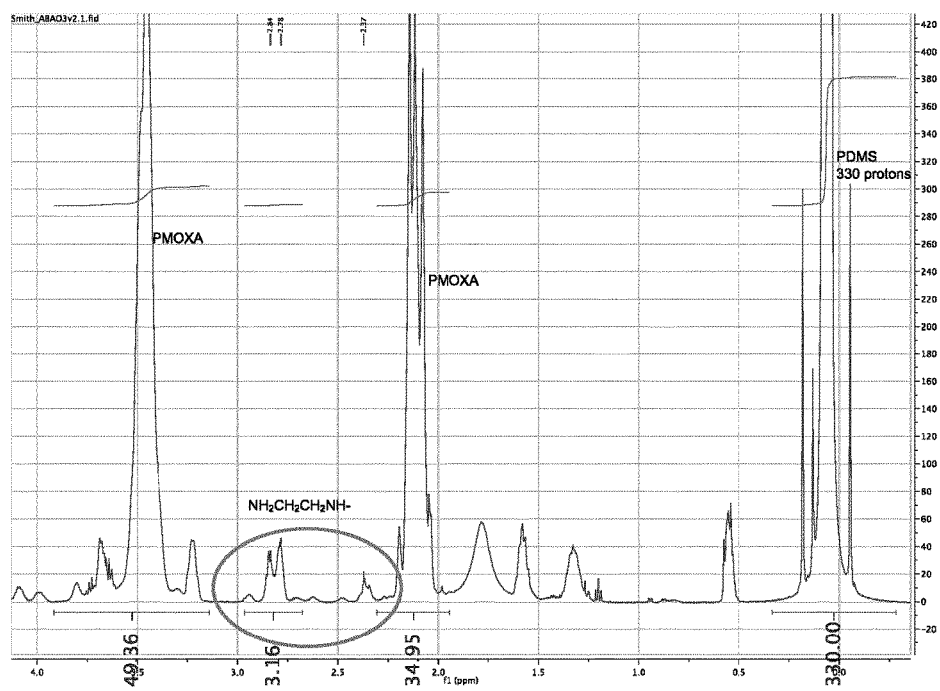
FIG. 1 shows the NMR spectrum of the product of Example 1.

In a three-neck round bottom flask 50 grams (0.012 mols) of PDMS were kept under high vacuum for 24 h. In the next step, a reaction flask was filled with dry argon, and the polymer was dissolved in dry hexane (200 ml) and added to the three-neck flask via septum. Cooled (0-5 deg C.) PDMS was than activated by drop-wise addition of 6.62 g (0.02346 mols) of trifluoromethanesulfonic anhydride in presence of 2.45 g (0.024 mols) of triethyl amine and allowed to post-react for 3 hours. The activated PDMS was further filtered under argon and hexane was removed under reduced pressure. 250 ml of dry ethyl acetate was added to re-dissolve the activated polymer, and ring-opening polymerization of 2-methyloxazoline was started upon addition of 23.5 g (0.27 mols) dried 2-methyl oxazoline at 40 deg C. After 12 hours reaction under argon, a 3-fold excess, 4.14 g (0.069 mols) of butyl-di-amine was added as terminating agent. Product was recovered under high vacuum and evaluated for molecular weight by proton NMR (FIG. 1) and molecular weight distribution by GPC in chloroform. The product was 100% soluble in ethanol and 99.5% insoluble in hexane. The remaining 0.5% was found to be unreacted PDMS as shown by proton NMR.

EXAMPLE 2

Materials:
ABA block-co-polymer, poly-2-methyl-2oxazoline-poly-dimethylsiloxane-poly-2-methyl-oxazoline, amine terminated, as prepared in Example 1
Aquaporin-Z stock solution 1 mg/ml in 1% octyl glucoside and 100 mM NaMPOS buffer at pH 7.5
100 mM NaMPOS buffer at pH 7.5
Chloroform (Puriss)
Octyl glucoside (Anatrace)
Amine functional polymer vesicles 10 mg/mL in Na.MOPS
PoPR (Polymer to Protein ratio, mass)
N-sulfosuccinimidyl-6-(4'-azido-2'-nitrophenylamino) hexanoate, sulfo-SANPAH (Pierce; Product No. 22589)
Dextrans (American Polymer Standards Corporation)
365 nm UV lamp (Entela UVP)
47 mm Membrane stamp
25 mm Membrane stamp
Polysulfone membrane; pore size 150 nm (cut-off over 1000 kDa)
1). Polymer Vesicles/Proteo-Vesicles Preparation:
50 mg of ABA block-co-polymer was dissolved in 2 ml of chloroform in a round bottom flask (Pyrex 100 ml). Chloroform was then removed under high vacuum to form a thin film of polymer. This film was hydrated with either 5 ml of buffer (control) or 5 ml of aqueous stock solution of Aquaporin-Z and stirred overnight. In these samples the amount of added protein was varied from 1:1 to 1:1200 polymer to protein ratio. Detergent was subsequently removed by dialysis in 30 kDa dialysis membranes in NaMOPS buffer. The resulting product was then extruded through track-etched membranes to uniform 200 nm size.

2). Coating

In this step, the concentration of deposited vesicles was kept constant and monitored by matching the count rate (250 kcps) in Dynamic Light Scattering (Malvern Zetasizer Nano) with static attenuator.

Sulfo-SANPAH (SS) solution (10 mM in 100 mM NaMOPS pH 7.5) was allowed to react with vesicles prepared as in step (1) in the absence of light (250 μL of vesicle solution combined with 50 μL SS for 15-minutes). A series of 47 mm polysulfone membranes (Nano H2O Inc, 150 nm) were cut by punch press and placed into Teflon membrane holders and rinsed with deionized water. Excess water was removed by compressed air and 300 μL (each) of SS-activated vesicles/proteo-vesicles solutions were placed onto polysulfone support membranes. The membrane holders were then placed under UV light approximately 5 cm from the source and covered with foil for protection for 30 minutes. Excess reactants were then removed from the membrane surface using a 1 ml pipette without touching the membrane surface. The above steps were repeated three times, following which the membranes were removed from the holders and 25 mm diameter membrane samples were cut from the coated area using a punch press. These were then rinsed in excess 100 mM NaMOPS ph7.5 on a shake table for at least one hour before testing.

3) Molecular Cut-Off Experiments

The 25 mm samples of step (2) tested for their ability to retain high molecular weight materials, by measuring their molecular weight cut-off, i.e. the point at which at least 90% of molecules of a given molecular weight are retained by the membrane.

Phosphate buffer (0.03M $Na_2HPO_4$+0.03M $KH_2PO_4$) was pre-filtered using a 0.2 um membrane and the pH was adjusted to 7.2 prior to use for preparation of solutions. Dextran (DXT) standards were dissolved in phosphate buffer (DXT 165 kDa, 325 kDa, 548 kDa, 1300 kDa, and 5000 kDa, DXT 0.505 kDa, 4 kDa, 6 kDa, 11 kDa, 20 kDa, and 28 kDa). All of the dextran solutions were diluted to 0.5 mg/ml with phosphate buffer and pre-filtrated using a 0.2 um PES membrane prior to use. All filtration experiments were conducted in a 10 ml Amicon stirred ultrafiltration cell (Model 8010, Millipore Corp.)

All samples were evaluated according to the protocol described below:

Filtered 10 ml volume of deionised water at 20 psi to wet the pore structure and the whole system.

Connected the feed line with dextran solution feed to a digital peristaltic pump (Thermal Fisher Science Inc.), re-pressurized the cell to 20 psi, set the filtrate flux to 5 μm/s.

Obtained 800 μL samples of the filtrate solution after filtration of 2,000 μL of water for equilibration and washing out the dead volume downstream of the membrane.

Obtained 1 ml permeate samples directly from the cell after filtration.

Cleaned and rinsed the whole system with deionised water.

The stirring speed was kept at 600 rpm and all experiments were performed at room temperature (22±3° C.)

Permeate was further evaluated using high-pressure liquid chromatography (HPLC columns PL1149-6840, MW 10,000 to 200,000, PL1120-6830, MW 100 to 30,000, PL1149-6860, MW 200,000 to >10,000,000). Comparison of the feed to the permeate chromatograms allowed for calculation of retention coefficients and membrane molecular cut-off.

Figure 2:
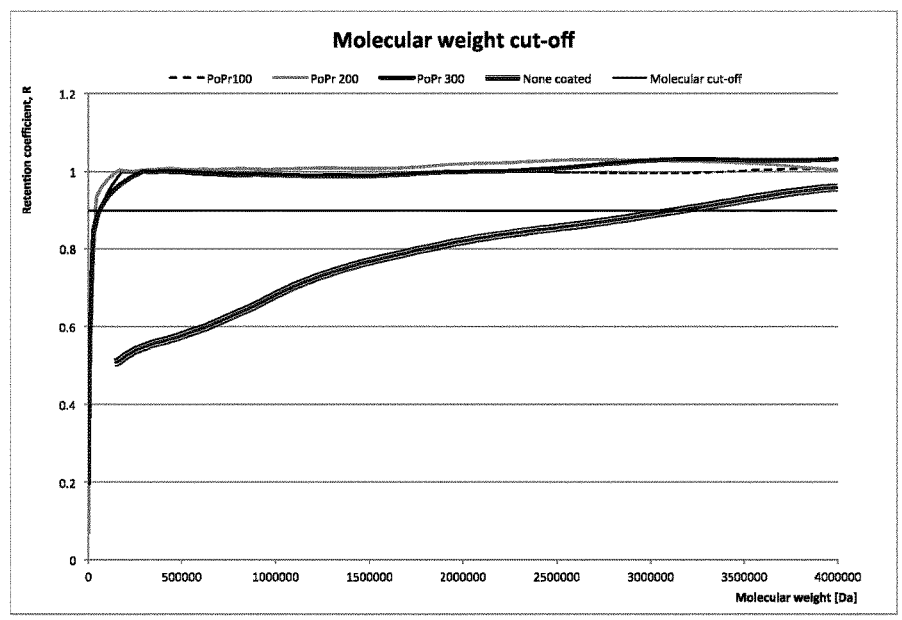
FIG. 2 shows the results of the molecular weight cut-off experiments of Example 2.

The results are shown in FIG. 2, which shows that all of the membranes according to the invention retained all of the higher molecular weight molecules, while the control membrane demonstrated significantly poorer performance, with a molecular weight cut-off in excess of 3,000 kDa.

4). Flow Testing

The 25 mm membranes of Step (2) were tested for their ability to transmit pure water using a stirred test cell (Amicon 10 ml, (Model 8010, Millipore Corp.) in which the feed was pure water. The system was closed and set to stir for at least 5 min before testing. Subsequently the pressure was gradually increased from 1 to 5 bar and data points representing the volume of pure water passing through the surface of the membrane in 1 minute were collected at 1 bar intervals (with permeate collected separately at each pressure). The experiment also included the best commercially available water filtration membrane currently on the market, Biomax 30 kDa from Millipore, for comparison.

Figure 3:
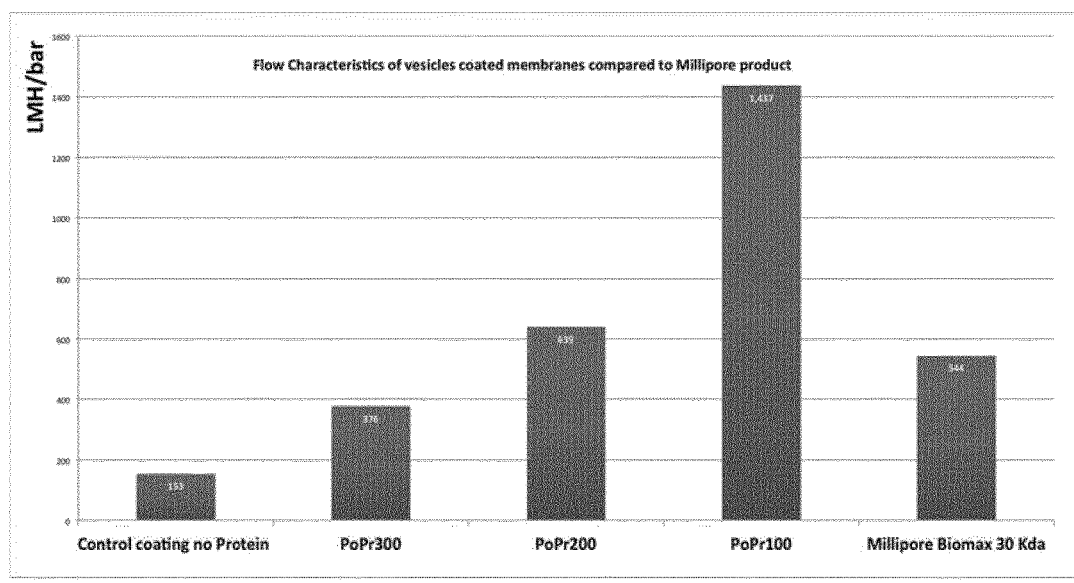
FIG. 3 shows the results of the flow testing experiments of Example 2.

The results are shown in FIG. 3, in which LMH/bar is liter/m$^2$/hour/bar of pure water, i.e. is a pressure-corrected flow rate, and PoPr represents polymer:protein ratio (note that the higher the PoPr, the lower the content of aquaporin protein).

The control membrane prepared in step 2 with a coating of vesicles but no aquaporin protein, had the lowest flow rate of all the membranes tested. All the membranes according to the invention performed significantly better, with a higher content of aquaporin leading to higher fluxes, and the membrane with the highest content of aquaporin significantly outperforming the commercially available membrane.

Figure 4:
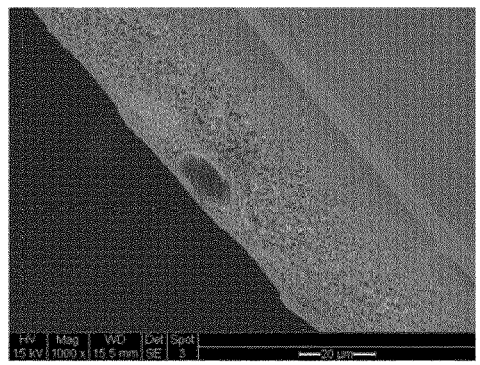
FIGS. 4 and 5 are scanning electron microscopy images of the membranes prepared in Example 2.
Figure 5:
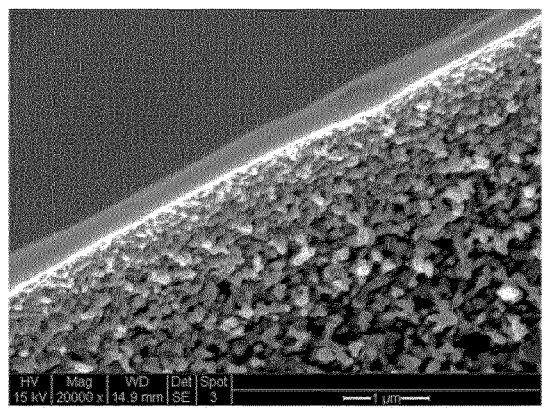

FIGS. 4 and 5 show SEMs of the membranes according to the invention. In FIG. 4 (magnification 1000) the lower layer having a sponge-like appearance is the polysulfone support, having a macrovoid due to the casting process. The upper layer is the continuous coating comprising a coherent mass of aquaporin-containing vesicles. In FIG. 5 (magnification 20,000), the lower portion of the SEM having a textured appearance is the polysulfone support, while the thin uppermost layer is the continuous coating comprising a coherent mass of aquaporin-containing vesicles. The bright line at the boundary between these two layers is a boundary layer where the vesicle layer is covalently bound to the polysulfone.

EXAMPLES 3 AND 4

Model experiments were carried out to confirm the suitability of various polymer end-groups for the preparation of vesicles and the covalent linking of vesicles to each other. The comparison polymers were prepared as follows.

(a) Carboxylic-Terminated poly-2-methyloxazoline-poly-di-methyl-siloxane-poly-2-methyloxazoline (PMOXA-PDMS-PMOXA)

Hydroxyl-terminated polymer Mn=4262 g/mol (PDMS) synthesized as in step (a) of Example 1 was used in the synthesis of poly PMOXA-PDMS-PMOXA amphiphilic block copolymer. In a three-neck round bottom flask 50 grams (0.01173 mols) of PDMS was kept under high vacuum for 24 h. In the next step reaction the flask was filled with dry argon and polymer was dissolved in dry hexane (200 ml) added to the three-neck flask via septum. Cooled (0-5 deg C.) PDMS was than activated by drop-wise addition of 6.62 g (0.02346 mols) of trifluoromethanesulfonic anhydride in presence of 2.45 g (0.024 mols) of triethylamine and allowed to post-react for 3 hours. The activated PDMS was then filtered under argon and hexane was removed under reduced pressure. 250 ml of dry ethyl acetate was added to re-dissolve the activated polymer and ring-opening polymerization of 2-methyloxazoline was started upon addition of 23.5 g (0.27 mols) dried 2-methyl oxazoline at 40 deg C. After 12 h reaction under argon, deprotonated malonic acid was added in 1.3× excess as terminating agent 3.12 g (0.030 mols) in the presence of triethylamine 3.05 g (0.030 mols). Product was recovered under high vacuum and evaluated for molecular weight by proton NMR and molecular weight distribution by GPC in chloroform.

(b) Hydroxy Terminated poly-2-methyloxazoline-poly-di-methyl-siloxane-poly-2-methyloxazoline (PMOXA-PDMS-PMOXA)

Hydroxyl-terminated silicon Mn=4262 g/mol (PDMS) synthesized as described in step (a) of Example 1 above was used in the synthesis of poly PMOXA-PDMS-PMOXA amphiphilic block copolymer.

In a three-neck round bottom flask 50 grams (0.01173 mols) of PDMS was kept under high vacuum for 24 h. In the next step reaction flask was filled with dry argon and polymer was dissolved in dry hexane (200 ml) added to the three-neck flask via septum. Cooled (0-5 deg C.) PDMS was then activated by drop-wise addition of 6.62 g (0.02346 mols) of trifluoromethanesulfonic anhydride in the presence of 2.45 g (0.024 mols) of triethylamine and allowed to post-react for 3 hours. The activated PDMS was then filtered under argon and hexane was removed under reduced pressure. 250 ml of dry ethyl acetate was added to re-dissolve activated polymer and ring-opening polymerization of 2-methyloxazoline was started upon addition of 23.5 g (0.27 mols) dried 2-methyl oxazoline at 40 deg C. After 12 h reaction under argon, potassium hydroxide was added in 1.3× excess as terminating agent (1.68 g (0.030 mols) in 50 ml of methanol). Product was recovered under high vacuum and evaluated for molecular weight by proton NMR and molecular weight distribution by GPC in chloroform.

EXAMPLE 3

Figure 6:
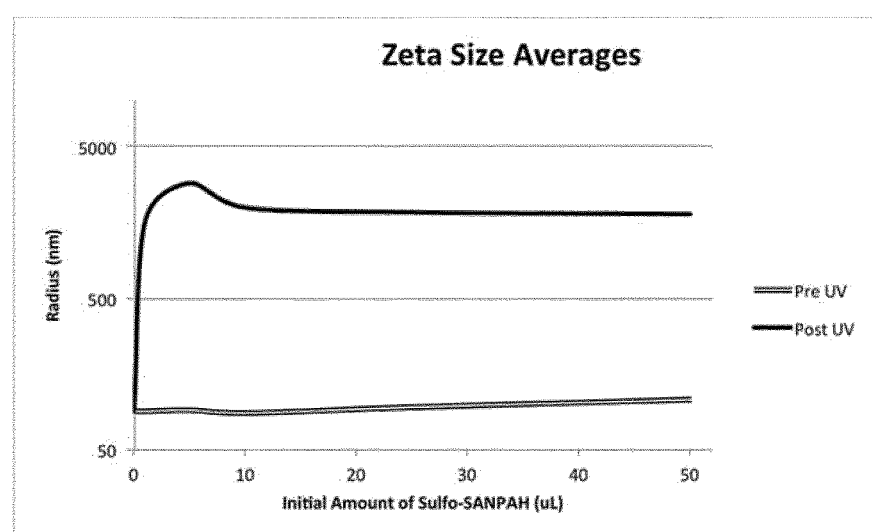
FIG. 6 shows the results of the dynamic light scattering measurements of Example 3.

250 µL of vesicles made from amine-terminated polymer as prepared in Example 1 were placed in a 64 mL clear glass vial, and protected from light by wrapping the vials in aluminum foil. The varying amounts (0, 1, 5, 10, 25 and 50 µl) of the difunctional linker sulfo-SANPAH, (10 mM Sulfo-SANPAH in 100 mM Na.MOPS pH 7.5) was added and mixed by gentle shaking. Reaction was allowed to take place for 15 minutes, following which 100 µL of solution was placed into a cuvette for dynamic light scattering (DLS) measurement, DLS being a technique for the measurement of the size of particles in solution. The sample was placed about 5 cm below the UV lamp, the lid and foil were removed, the lamp was switched on, and the whole was covered with a foil tent. In all cases the attenuator was fixed at 6. After 15 minutes under UV, Prior to reaction with sulfo-SANPAH, DLS showed the diameter of the vesicles to be 200 nm. After UV irradiation to cause reaction with sulfo-SANPAH, large aggregates were formed which could be seen with the naked eye. The DLS results are shown in FIG. 6. These aggregates were stable under sonication, indicating the presence of covalent bonding.

As a comparison, a similar experiment was carried out using hydroxyl-terminated polymer, which is not expected to be reactive with sulfo-SANPAH. As expected, no cross-linking occurred, and therefore no increase in diameter measured by DLS occurred.

EXAMPLE 4

Experiments were carried out using vesicles made from polymers having activated carboxylic acid groups as end groups.

Materials
  EDC, Pierce (Product No. 22980)
  NHS, Pierce (Product No. 24500)
  Malvern Zetasizer NANO DLS
  Sonication Bath
  pH Meter with micro probe
  Carboxyl terminated polymer vesicles prepared as described above
  Amine terminated polymer vesicles prepared as described above Experimental
  Vesicles were prepared according to above described thin-film hydration protocol using deionised water. The average diameter of the resulting polymer vesicles was shown to be around 200 nm using DLS.
  Carboxylic vesicles activated with EDC and NHS were prepared by addition of 950 µg of EDC and 570 µg of NHS to 1 ml of carboxylic vesicles. The solution was then adjusted to pH 5 using HCl and allowed to react for 30 minutes at room temperature resulting in EDC-NHS activated vesicles.
  Solutions of (control) carboxylic vesicles (1 ml) and EDC-NHS activated vesicles (1 ml) were allowed to react with equal amount of amine-functional vesicles (1 ml). Subsequently the pH of all solutions was adjusted about 7.5 with a dilute solution of NaOH in deionised water and allowed to react for at least 90 minutes. 100 µL of the resulting samples were tested by DLS using a static attenuator setting of 5. After testing, the cuvettes were sonicated for 1 minute and then retested.
  It was found that reaction of equal amounts of amine and carboxylic vesicles resulted in the formation of large aggregates (around 2000 nm by DLS). However, when sonicated, these aggregates dispersed, showing that the bonding was ionic rather than covalent. In contrast, reaction of equal amounts of amine and EDC-NHS activated carboxylic vesicles resulted in formation of large aggregates (about 3600 by DLS) which were not dispersed when sonicated, indicating that the forces holding aggregates together were covalent.

EXAMPLE 5—VESICLE FORMATION

Vesicles were prepared from the amine-terminated polymer of step b of Example 1 above by the method described in Example 2, save that no aquaporin protein was added. Well-defined vesicles were formed, and are shown in FIGS. 7A and 7B.

EXAMPLE 6—VESICLE FORMATION (COMPARATIVE)

Example 5 was repeated using the hydroxy-terminated polymer prepared as described above. In contrast to Example 5, vesicles were not formed: rather, micelles of much smaller size were formed, and are shown in FIGS. 8A and 8B.

The invention claimed is:

1. A block copolymer comprising at least one (poly)2-$C_{1-3}$alkyl-2-oxazoline block and at least one (poly)dimethyl siloxane block, having at least one end group X which includes both an —$NH_2$ group and an —NH— group.

2. A block copolymer as claimed in claim 1, in which the end group has the formula —NHR in which R represents an alkyl group having from 1 to 6 carbon atoms substituted by at least one —$NH_2$ group.

3. A block copolymer as claimed in claim 2, in which the end group has the formula —NH—CH—$(NH_2)_2$ or —NH—$(CH_2)_n$—$NH_2$, in which n is an integer from 2 to 6.

4. A block copolymer as claimed in claim 3, in which the end group has the formula —NH—$(CH_2)_n$—$NH_2$, in which n is an integer from 2 to 6.

5. A block copolymer as claimed in claim 4, in which n is 2.

6. A block copolymer as claimed in claim 1, which is a triblock copolymer having two outer (poly)2-$C_{1-3}$alkyl-2-oxazoline blocks and an inner (poly)dimethyl siloxane block.

7. A block copolymer as claimed in claim 1, in which the or each (poly)dimethyl siloxane block has a mean molecular weight of from 500 to 50,000 g/mol.

8. A block copolymer as claimed in claim 1, in which the or each poly(2-$C_{1-3}$ alkyl-2-oxazoline block has a mean molecular weight of from 200 to 50,000 g/mol.

9. A block copolymer as claimed in claim 6, in which the (poly)dimethyl siloxane block contains from 20 to 150 dimethyl siloxane units and each (poly)2-$C_{1-3}$alkyl-2-oxazoline block contains from 10 to 100 2-$C_{1-3}$alkyl-2-oxazoline units.

10. A block copolymer as claimed in claim 1, in which said (poly)2-$C_{1-3}$alkyl-2-oxazoline block is a (poly)2-methyl-2-oxazoline block.

11. A vesicle formed from a block copolymer as claimed in claim 1.

12. A vesicle as claimed in claim 11, having transmembrane proteins incorporated therein.

13. A vesicle as claimed in claim 12, in which the transmembrane protein is an aquaporin.

14. A filtration membrane which comprises a porous support and, covalently bonded to a surface thereof, a layer comprising a plurality of vesicles having transmembrane proteins incorporated therein, said vesicles being formed from a block copolymer comprising at least one (poly)2-$C_{1-3}$alkyl-2-oxazoline block and at least one (poly)dimethyl siloxane block; characterised in that within said layer, vesicles are covalently linked together to form a coherent mass, at least some of said covalent linkages having been formed from —$NH_2$ groups present in a vesicle as claimed in claim 12.

15. A vesicle as claimed in claim 11, containing a drug.

16. A process for the preparation of a filtration membrane as claimed in claim 14, which comprises providing an aqueous suspension of vesicles as claimed in claim 12; depositing said suspension of vesicles on a surface of a porous support; and providing reaction conditions such that covalent bonds are formed between different vesicles and between vesicles and said surface.

17. A process for the preparation of a filtration membrane as claimed in claim 14, which comprises either:
(A) (a) providing a first aqueous suspension of vesicles as claimed in claim 12;
(b) providing a second aqueous suspension of vesicles having transmembrane proteins incorporated therein, said vesicles being formed from block copolymers comprising at least one (poly)2-$C_{1-3}$alkyl-2-oxazoline block and at least one (poly)dimethyl siloxane block and having end groups Y which are reactive with the polymer end groups X present in the vesicles of step (a);
(c) depositing said suspensions of vesicles on a support having a surface which is reactive with either polymer end groups X or Y; and
(d) causing reaction of end groups X with end groups Y, and either end groups X or end groups Y with the surface of the support; or
(B) (a) providing an aqueous suspension of vesicles as claimed in claim 12;
(b) providing an multifunctional linking agent having at least two reactive groups Y which are reactive with polymer end groups X of the vesicles of step (a);
(c) depositing said suspension of vesicles and said multifunctional linker on a support having a surface which is reactive with either polymer end groups X or reactive groups Y; and
(d) causing reaction of end groups X with groups Y, and either end groups X or groups Y with the surface of the support.

18. A process as claimed in claim 17, in which groups Y are carboxylic acid, activated carboxylic acid, and/or azide groups.

19. A process as claimed in claim 17, in which said multifunctional linking agent comprises one group Y which is an activated carboxylic acid group and another group Y which is an azide group.

20. A process as claimed in claim 19, in which the multifunctional linking agent is N-sulfosuccinimidyl-6-(4'-azido-2'-nitrophenylamino)hexanoate.

* * * * *